(12) United States Patent
Marin et al.

(10) Patent No.: US 12,117,674 B2
(45) Date of Patent: Oct. 15, 2024

(54) METHOD FOR DETERMINING A VALUE OF A GLOBAL SENSITIVITY PARAMETER OF A SUBJECT, METHODS USING THIS VALUE AND SYSTEM FOR DETERMINING SAID VALUE

(71) Applicant: Essilor International, Charenton le Pont (FR)

(72) Inventors: Gildas Marin, Charenton le Pont (FR); Martha Hernandez-Castaneda, Charenton le Pont (FR); Laurent Calixte, Charenton le Pont (FR); Adèle Longo, Charenton le Pont (FR); Cyril Guilloux, Charenton le Pont (FR)

(73) Assignee: Essilor International, Charenton-le-Pont (FR)

( * ) Notice: Subject to any disclaimer, the term of this patent is extended or adjusted under 35 U.S.C. 154(b) by 941 days.

(21) Appl. No.: 17/261,479

(22) PCT Filed: Jul. 19, 2019

(86) PCT No.: PCT/EP2019/069472
§ 371 (c)(1),
(2) Date: Jan. 19, 2021

(87) PCT Pub. No.: WO2020/016398
PCT Pub. Date: Jan. 23, 2020

(65) Prior Publication Data
US 2021/0311325 A1    Oct. 7, 2021

(30) Foreign Application Priority Data

Jul. 20, 2018   (EP) ..................................... 18305996

(51) Int. Cl.
*G02C 7/02* (2006.01)
*A61B 3/00* (2006.01)

(52) U.S. Cl.
CPC ............ *G02C 7/027* (2013.01); *A61B 3/0025* (2013.01); *A61B 3/0041* (2013.01)

(58) Field of Classification Search
CPC ...... G02C 7/027; A61B 3/0025; A61B 3/0041
(Continued)

(56) References Cited

U.S. PATENT DOCUMENTS

| 2003/0053025 A1* | 3/2003 | Turner ...................... A61F 2/16 351/205 |
| 2003/0107706 A1* | 6/2003 | Rubinstein ............. G02C 7/061 351/159.77 |

(Continued)

FOREIGN PATENT DOCUMENTS

| CN | 102165362 A | 8/2011 |
| CN | 102460273 A | 5/2012 |

(Continued)

OTHER PUBLICATIONS

International Search Report for PCT/EP2019/069472 dated Oct. 17, 2019, 4 pages.

(Continued)

*Primary Examiner* — James R Greece
(74) *Attorney, Agent, or Firm* — NIXON & VANDERHYE

(57) ABSTRACT

Disclosed is a hoist apparatus including: an electric motor, and a control box that can be electrically powered by a power supply, the control box including at least an electronic control circuit, an electrical wiring and an external casing forming a box of the control box, the external casing including at least sidewalls and a removable lid closing the box, the control box controlling the operations of the electric motor thanks to the electrical wiring connected to the electronic control circuit, to the power supply and to the electric motor, and a monitoring device, wherein the moni- (Continued)

toring device is an insert of the box, the monitoring device being arranged within an enclosure, the enclosure being an added part of the box or being an exchanged part of the box and wherein the monitoring device is connected to the electrical wiring.

20 Claims, 9 Drawing Sheets

(58) Field of Classification Search
 USPC .................................................. 351/159.74
 See application file for complete search history.

(56) References Cited

U.S. PATENT DOCUMENTS

| | | |
|---|---|---|
| 2005/0088616 A1 | 4/2005 | Nason et al. |
| 2016/0331226 A1 | 11/2016 | Nauche et al. |
| 2017/0027435 A1 | 2/2017 | Boutinon et al. |

FOREIGN PATENT DOCUMENTS

| | | | |
|---|---|---|---|
| CN | 102483527 A | 5/2012 | |
| EP | 2 348 350 | 7/2011 | |
| EP | 2348350 A1 * | 7/2011 | ............... G02C 7/00 |
| EP | 3 006 991 | 4/2016 | |
| EP | 3 088 938 | 11/2016 | |
| FR | 3 051 262 | 11/2017 | |
| JP | 2004-283271 A | 10/2004 | |
| JP | 2017-531827 A | 10/2017 | |
| WO | 2010/035726 A1 | 4/2010 | |
| WO | 2011/001082 A2 | 1/2011 | |
| WO | 2015/099135 A1 | 7/2015 | |
| WO | 2016/055265 A1 | 4/2016 | |
| WO | 2017/021663 | 2/2017 | |
| WO | 2017/194898 | 11/2017 | |
| WO | 2018/015381 | 1/2018 | |

OTHER PUBLICATIONS

Written Opinion of the ISA for PCT/EP2019/069472 dated Oct. 17, 2019, 7 pages.
Office Action issued in Japanese Patent Application No. 2021-503068 dated Mar. 6, 2023.
Office Action issued in Chinese Patent Application No. 201980048166.1 dated Mar. 22, 2022.
Blendowske, "Unaided Visual Acuity and Blur: A Simple Model," Optometry and Vision Science, vol. 92, No. 6, 2015, pp. e121-e125.
Fauquier et al., "Influence of combined power error and astigmatism on visual acuity," Ophthalmic and visual optics Technical Digest, Optical Society of America, Washington, D.C., vol. 1, 1995, pp. 151-154.
Gomez-Pedrero and Alonso, "Phenomenological model of visual acuity," Journal of Biomedical Optics, vol. 21, No. 12, Dec. 2016, pp. 125005-1 to 125005-9.
Le Grand, "On the Calculation of Eye Lenses," Journal of Optic, 1966, 6 pages.

* cited by examiner

Fig.3
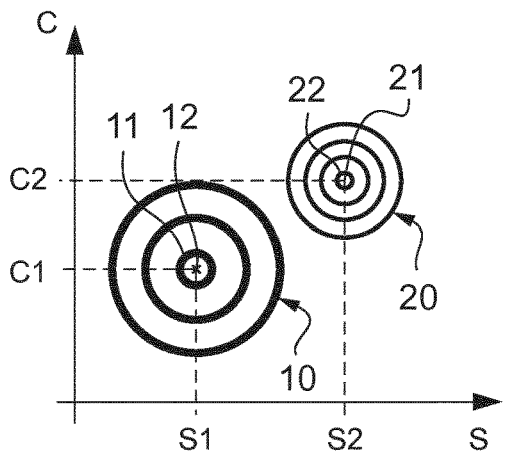
Fig.4
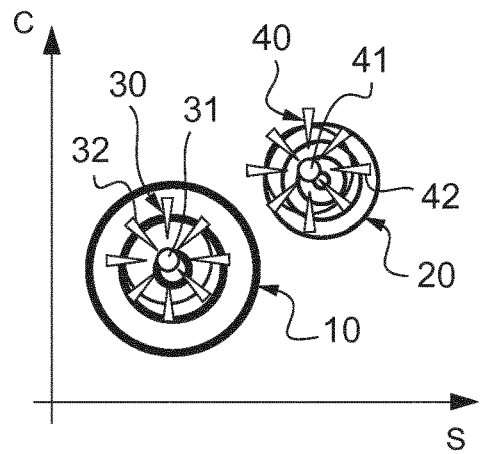
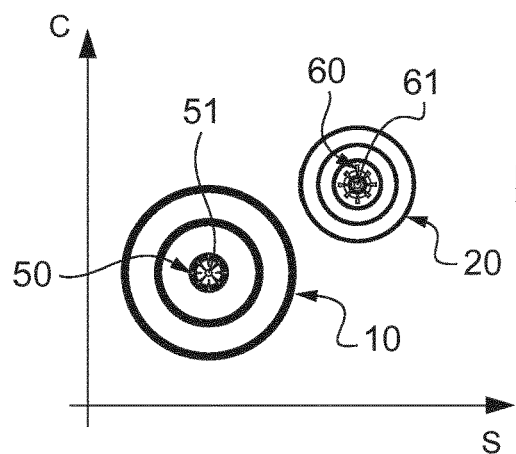
Fig.5
Fig.6
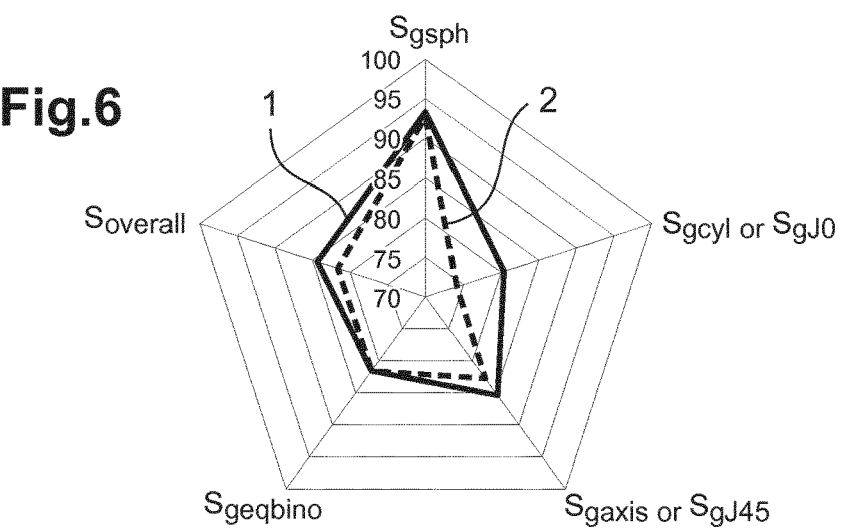

METHOD FOR DETERMINING A VALUE OF A GLOBAL SENSITIVITY PARAMETER OF A SUBJECT, METHODS USING THIS VALUE AND SYSTEM FOR DETERMINING SAID VALUE

CROSS-REFERENCE TO RELATED APPLICATIONS

This application is the U.S. national phase of International Application No. PCT/EP2019/069472 filed Jul. 19, 2019 which designated the U.S. and claims priority to EP 18305996.3 filed Jul. 20, 2018, the entire contents of each of which are hereby incorporated by reference.

TECHNICAL FIELD OF THE INVENTION

The invention relates to a method for determining a value of a global sensitivity parameter of a subject.

It also relates to a method for determining an optical feature of an ophthalmic lens adapted to improve the vision of a subject, a method for informing an eye care practitioner of the value of a global sensitivity parameter of a subject, a method for selecting an appropriate optical design of an ophthalmic lens adapted to improve the vision of a subject and a method for modifying a predetermined optical design for an ophthalmic lens in order to adapt it to the vision of a subject, taking into account this value of a global sensitivity parameter for said subject.

It also relates to a system for performing this method.

BACKGROUND INFORMATION AND PRIOR ART

Document WO2018/015381 describes a method for determining single values of specific sensitivity parameter for one eye of a subject. These single specific sensitivity parameters are relative to the sensitivity of the eye of the subject to a variation of a specific optical feature of a lens placed in front of this eye.

This single specific sensitivity parameter is related to the smallest variation of the specific optical feature that may be perceived by the subject.

In practice, it may be defined as the range of values of the specific optical feature that could be acceptable or for which the subject cannot decide which one is better.

The single values of the specific sensitivity parameters determined for different specific optical features such as sphere, cylinder or axis, addition, and for each of the eyes of the subject may be different. Moreover, the single values determined may suffer from a measurement uncertainty.

Based on the single values of these specific sensitivity parameters, it is therefore impossible to deduce general information about the subject's sensitivity to an error in the determination of the corresponding optical feature of a lens adapted to improve this subject's vision or to an optical aberration of a lens having the optical feature adapted to improve this subject's vision.

SUMMARY OF THE INVENTION

Therefore one object of the invention is to provide a method for determining a reliable value of a global sensitivity parameter providing a global evaluation of the sensitivity of a subject to variation of at least an optical feature of at least one ophthalmic lens.

By reliable, it is meant that the values of the global sensitivity parameter represent better the sensitivity of the subject. They are more repeatable.

The above objects are achieved according to the invention by providing a method for determining the value of a global sensitivity parameter of a subject, said global sensitivity parameter being relative to the sensitivity of said subject to a variation of at least a dioptric optical feature of at least an ophthalmic lens placed in front of at least one eye of said subject, comprising the following steps:
  a) determining a single value of at least a first sensitivity parameter of said subject, relative to the sensitivity of the subject to a variation of a first dioptric optical feature of at least a first ophthalmic lens,
  b) determining a single value of at least a second sensitivity parameter of said subject relative to the sensitivity of the subject to a variation of a second dioptric optical feature of at least a second ophthalmic lens,
  each of the first and second sensitivity parameters being respectively related to the smallest variation of said first and second dioptric optical feature that may be perceived by the subject,
  c) using computing means to determine said value of the global sensitivity parameter taking into account a combination of said single values of the first and second sensitivity parameters.

The value of the global parameter thus determined is more reliable to assess the sensitivity of the subject than the single values of the first and second sensitivity parameters. It may either reflects:
  a global sensitivity of one of the eyes to variations of one or several optical features of one lens placed in front of this eye, in the same or different environmental conditions,
  a global sensitivity of both eyes to independent variations of one or several optical feature of each lens placed in front of one of the eyes, in the same or different environmental conditions,
  an global sensitivity of both eyes to a variation of one or several optical features of a couple of lenses placed in front of the eyes, in the same or different environmental conditions.

In the last case, the variation may be absolute or relative: it may be a variation in the corresponding optical feature of each of both lenses or a variation in the difference between the optical features of both lenses.

The value of the global sensitivity parameter may also be taken into account as a tolerance during the whole processing chain: determination of the refraction; during the refraction test protocol, determination of the best next visual test to propose to the subject; prescription of the correction needed; manufacturing and/or edging/mounting up to delivery in optician stores; adjustment of the frame of the head of the subject and finally used to advise a renewal/visual check frequency.

The value of the global sensitivity parameter may also be taken into account when choosing a frame, by selecting an adequate pantoscopic angle, wrap angle . . . .

It is a decision support for eye care practitioner in case of patients with difficult problems (amblyopia, strong dominance, anisometropia . . . ), in order to give the patient the prescription the most adapted to his specific problem.

Other advantageous and non limitative features of the method according to the invention are the following:
  said at least a first and second sensitivity parameters determined in step a) and b) each comprises at least one of the following:

sphere sensitivity to the variation of sphere of said at least a first or second ophthalmic lens for at least one of the eyes of said subject, cylinder and/or axis sensitivity to the variation of cylinder power and/or axis of said at least a first or second ophthalmic lens for at least one of the eyes of the subject, sphere binocular sensitivity of said subject to the binocular variation of the sphere of the first and second ophthalmic lenses, binocular balance sensitivity of the subject to a variation in binocular balance of the first and second ophthalmic lenses, addition sensitivity to the variation in the addition of said at least a first or second ophthalmic lens for at least one of the eyes of the subject;

said single values of at least a first and second sensitivity parameters determined in step a) and b) are each determined with different measuring methods or each determined in similar or different measurement conditions;

in step c), said combination comprises a mean of the single values of the first and second sensitivity parameters determined during steps a) and b);

the single values of the first and second sensitivity parameters determined during step a) and b) are either:

single values of the cylinder sensitivities (ScylOG, ScylOD) of each of the left and right eyes or single values the axis sensitivities (SaxisOG, SaxisOD) of each of the left and right eyes, or single values of astigmatism sensitivities (Sasr, SJ0, SxJ0, SJ45, SxJ45) of each of the left and right eyes, single values of the sphere, cylinder, axis and binocular balance sensitivities of one of the left (SsphOG, ScylOG, SaxisOG, Seqbino) and right (SsphOD, ScylOD, SaxisOD, Seqbino) eyes, and, in step c), the value of the global sensitivity parameter determined is respectively the value of a global cylinder sensitivity parameter (Sgcyl) equal to the mean value of the single values of the cylinder sensitivities of the left and right eyes or the value of a global axis sensitivity parameter (Sgaxis) equal to a mean value of the single values of the axis sensitivities of the left and right eyes or the value of a global left or right eye sensitivity parameter (SgOG, SgOD) equal to the mean value of the single values of the sphere, cylinder, axis and binocular balance sensitivities of the left or right eyes;

during step a) and b), single values of the sphere sensitivity (SsphOG, SsphOD) of each of the left and right eyes of the subject and a single value of the sphere binocular sensitivity (Sphbino) of said subject are determined, and, in step c), the value of the global sensitivity parameter determined is the value of a global sphere sensitivity parameter (Sgsph) equal to a mean value of the single values of the sphere sensitivities of the left and right eyes and of the sphere binocular sensitivity;

during step a) and b), the following are determined:

single values of the sphere sensitivities (SsphOD, SsphOG) of each of the left and right eyes, and single values of the cylinder sensitivities (ScylOD, ScylOG) of each of the left and right eyes, and single values of the axis sensitivities (SaxisOD, SaxisOG) of each of the left and right eyes, and a value of the sphere binocular sensitivity (Ssphbino) of said subject, and a value of the binocular balance sensitivity (Seqbino) of said subject, and in step c), a value of a final global sensitivity parameter Sgfinal is determined with the following equation:

$$Soverall=[(SsphOD+SsphOG+Ssphbino)/3+(ScylOD+ScylOG)/2+(SaxOD+SaxOG)/2+Seqbino]/4;$$

in step c), said combination comprises a weighted mean value of the single values of the first and second sensitivity parameter determined during steps a) and b), the weights associated to the values of the first and second sensitivity parameters depending on:

a usual visual behavior of the subject, and/or a type of lens to be worn by the subject, and/or activities that the subject wishes to have with the lens, and/or an eye dominance data, and/or an assessment of the comfort of a current/previous lens worn by the subject, and/or data indicated on the previous prescription for an optical correction equipment;

it further comprises a step of displaying this value of the global sensitivity parameter for informing an eye care practitioner;

during step a) and b), a value of the binocular balance sensitivity of the subject is determined, and in step c), a value of a final global sensitivity parameter is determined as a mean value of the values of the global sphere sensitivity parameter, the global cylinder sensitivity parameter and the global axis sensitivity parameter and the value of the binocular balance sensitivity;

in step c), said combination of said values of the first and second sensitivity parameters comprises a weighted mean value of the values of the first and second sensitivity parameter determined during steps a) and b) and said weights are higher for the values of the parameters relative to the dominant eye of the subject than the weights associated to the values of the parameters relative to the non dominant eye of the subject, or said weights are higher for the values of the cylinder and axis sensitivity of each eye than the weights associated to the values of the sphere sensitivity of each eye if the subject is a progressive lens subject.

The invention also relates to a method for determining an adapted optical feature of an ophthalmic lens adapted to improve the vision of a subject, in near, an/or intermediate and/or far distances comprising the following steps:

performing a test protocol comprising repeated steps of:

placing a test lens in front of an eye of the subject, assessing the quality of vision of the subject looking through said test lens, the value of the dioptric optical feature of the test lens being incremented by a incremental value between each repetition of said steps, comparing the quality of vision of the subject looking through at least two successive test lenses placed in front of the eye of the subject during two successive repetition of said steps of the test protocol, and determining said adapted dioptric optical feature based on this comparison, determining a value of a global sensitivity parameter of a subject according to the method described above, determining said incremental value taking into account this value of the global sensitivity parameter.

Optionally, said incremental value is determined to minimize the difference between this incremental value and the value of the global sensitivity parameter.

It also relates to a method for selecting an appropriate optical design for an ophthalmic lens adapted to improve the vision of a subject, among a list of predetermined optical designs, said optical design comprising current values of at least one dioptric optical feature of the corresponding lens having said predetermined optical design, associated with a plurality of gaze directions of the subject when the lens is worn by said subject, comprising the following steps:

determining a value of a global sensitivity parameter of a subject according to the method described above, determining an adapted value of said dioptric optical feature adapted to improve the vision of the subject, determining, for different gaze directions, the difference between the current value of the dioptric optical feature of the corresponding lens and the adapted value of said dioptric optical feature, comparing this difference with the value of the global sensitivity parameter of the subject, selecting, among said list of predetermined optical designs, the appropriate optical design taking into account this comparison.

This method may further comprise:

determining a region of said predetermined optical design for which said difference is smaller than the value of the global sensitivity parameter of the subject, selecting the appropriate optical design by selecting the optical design having the region with a larger size in at least one predetermined direction, and/or having a shape closer to a predetermined shape.

It also relates to a method for modifying a predetermined optical design for an ophthalmic lens in order to adapt it to the vision of a subject, said optical design comprising the current values of at least one dioptric optical feature of a corresponding lens having said predetermined optical design, associated with a plurality of gaze directions of the subject when the lens is worn by said subject, comprising the following steps:

determining a value of a global sensitivity parameter of a subject according to the method described above, determining an adapted value of said dioptric optical feature adapted to improve the vision of the subject, determining, for several gaze directions, the difference between the current value of the dioptric optical feature of the corresponding lens and the adapted value of said dioptric optical feature, comparing this difference with the value of the global sensitivity parameter of the subject, determining a modified optical design for a modified corresponding lens by modifying said predetermined optical design of the lens taking into account this comparison.

This method may further comprise:

determining a region of said predetermined optical design for which said difference is smaller than the value of the global sensitivity parameter of the subject, determining said modified optical design in order for a modified region of the modified optical design for which said difference is smaller than the value of the global sensitivity parameter of the subject to be larger in comparison to the size of said region in the predetermined optical design and/or to have a shape closer to a predetermined shape.

It also relates to a system for determining a value of a global sensitivity parameter of a subject, said global sensitivity parameter being relative to the sensitivity of said subject to a variation of at least a dioptric optical feature of at least an ophthalmic lens placed in front of at least one eye of said subject, comprising:

means for determining a single value of at least a first sensitivity parameter of said subject, relative to the sensitivity of the subject to a variation of a first dioptric optical feature of at least a first ophthalmic lens, means for determining a single value of at least a second sensitivity parameter of said subject, relative to the sensitivity of the subject to a variation of a second dioptric optical feature of at least a second ophthalmic lens, computing means programmed for determining said value of the global sensitivity parameter taking into account a combination of said single values of the first and second sensitivity parameters.

It may further comprise:

means for storing said value of the global sensitivity parameter determined by the computing means, and/or means for displaying said value of the global sensitivity parameter determined by the computing means.

DETAILED DESCRIPTION OF EXAMPLE(S)

The following description, enriched with joint drawings that should be taken as non limitative examples, will help understand the invention and figure out how it can be realized.

On joint drawings:

FIGS. 3 to 6 show different manners of displaying the values of different global sensitivity parameters;

FIG. 1 show a schematic block diagram of the steps to be performed according to one embodiment of the method for determining a value of a global sensitivity parameter of at least one eye of a subject. This global sensitivity parameter is relative to the sensitivity of said subject to a variation of at least an optical feature of at least an ophthalmic lens.

The optical features considered comprise in particular dioptric features of a lens or a couple of lenses measured in diopters. They comprise in particular the optical powers such as sphere, cylinder, astigmatism, addition, binocular balance, binocular sphere . . . .

The global sensitivity parameter may be relative to the sensitivity of said subject to a variation of one specific optical feature of a lens, such as sphere or cylinder or axis or addition, for one eye of said subject; to a variation of only one specific optical feature of a lens, such as sphere or cylinder or axis or addition, for both eyes of said subject, or to a binocular variation of one specific optical feature of a couple of lenses, such as the binocular values of the sphere or the binocular balance of the sphere of the couple of lenses, for both eyes of the subject.

It may be relative to the sensitivity of said subject to the variation of different specific optical features of a single lens, such as sphere and/or cylinder and/or axis and/or addition for the same eye of the subject; to a variation of different specific optical features of a single lens, such as sphere and/or cylinder and/or axis or addition, for each eye of said subject or to a binocular variation of different specific optical features of a couple of lenses, such as the binocular values of the sphere or the binocular balance of the sphere of the couple of lenses, for both eyes of the subject.

The first and second sensitivity parameters may each be determined with different measuring methods or each be determined in similar or different measurement conditions.

In an embodiment, the global sensitivity parameter may either be relative to the sensitivity of said subject to a variation of at least two different optical features for only one eye of the subject, or it may be relative to the sensitivity of said subject to the variation of at least one optical feature taking into account each eye of the subject.

Figure 1:
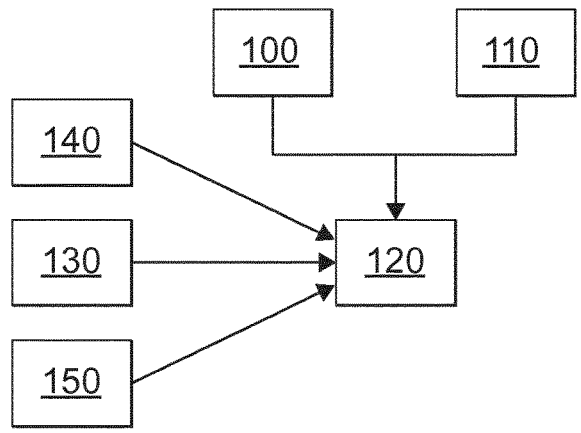
FIG. 1 is a block diagram schematically showing the steps for determining the global sensitivity parameter according to an example of the method of the invention.

The method for determining the value of this global sensitivity parameter of the subject according to the invention comprises the following steps:
a) determining a single value of at least a first sensitivity parameter of said subject, relative to the sensitivity of the subject to a variation of a first dioptric optical feature of at least a first ophthalmic lens (block 100 of FIG. 1),
b) determining a single value of at least a second sensitivity parameter of said subject relative to the sensitivity of the subject to a variation of a second dioptric optical feature of at least a second ophthalmic lens (block 110 of FIG. 1),
each of the first and second sensitivity parameters being respectively related to the smallest variation of said first and second dioptric optical feature that may be perceived by the subject,
c) using computing means to determine said value of the global sensitivity parameter taking into account a combination of said single values of the first and second sensitivity parameters (block 120 of FIG. 1).

Steps a) and b) may be performed by the same or different means. Each of these steps may be performed on the same day or at different moment in time. The determination of a single value of a sensitivity parameter may be based on a measurement, as described later, or on the retrieval of a value previously determined. The method may comprise a step of transmitting the values determined in steps a) and b) to computing means that perform step c).

In the following, optical features of the lens are dioptric optical features, as described hereafter.

The method may further comprise
a step of storing said value of the global sensitivity parameter determined by the computing means, and/or
a step of displaying said value of the global sensitivity parameter determined by the computing means.

Step a) and b)

Each of the first and second sensitivity parameters are respectively related to the smallest variation of said first and second dioptric optical feature that may be perceived by the subject.

Each of the first and second sensitivity parameters is relative
to the specific sensitivity of said subject to the variation of one of the optical features of a lens, said variation being perceived with one of the eyes of the subject, or
to the specific sensitivity of said subject to the variation of one of the optical features of a couple of lenses, said variation being perceived with both eyes of the subject.

More precisely, said at least a first and second sensitivity parameters determined in step a) and b) each comprises at least one of the following:
sphere sensitivity to the variation of sphere of said at least a first or second ophthalmic lens for at least one of the eyes of said subject,
cylinder and/or axis sensitivity to the variation of cylinder power and/or axis of said at least a first or second ophthalmic lens for at least one of the eyes of the subject,
sphere binocular sensitivity of said subject to the binocular variation of the sphere of the first and second ophthalmic lenses,
binocular balance sensitivity of the subject to a variation in binocular balance between the first and second ophthalmic lenses,
addition sensitivity to the variation in the addition of said at least a first or second ophthalmic lens for at least one of the eyes of the subject.

Moreover, optionally, said at least a first and second sensitivity parameters determined in step a) and b) may each be determined with different measuring methods or each be determined in similar or different measurement conditions.

A method is known and described in document WO2018/015381 for determining single values of specific sensitivity parameters for one eye of a subject.

During a complete process of refraction, each single value of specific sensitivity parameter is measured as described in this document, for each eye.

More precisely, each specific sensitivity parameter for one eye of the subject is representative of the smallest variation of the corresponding specific optical feature of a lens placed in front of this eye of the subject that is perceived by the subject, based on this subject's subjective assessment.

In practice, the subject's vision is tested during a test protocol, using a phoropter allowing to place successively in front of his eye lenses with different values of said specific optical feature.

This test protocol may be achieved using a classical phoropter or a phoropter having two complexe lenses of variable power.

In a classical phoropter, different lenses with a fixed, predetermined power may be place successively in front of each eyes of the subject. For example, lenses with different sphere are placed successively in front of one of the eyes of the subject. The sphere is increased by a predetermined step from one lens to the next. The step is typically of 0.25 diopter (D), or 0.125 D.

Said test protocol may also use an improved phoropter including lenses of variable power. Such phoropter/variable lenses are for example described in the following documents: US20160331226, US2017027435 or WO2017/021663.

For each current lens placed in front of his eye, the subject is asked to assess the quality of his vision through the current lens as compared to the previous lens: he is asked to express a visual assessment that corresponds to an indication of a preferred visual state among two visual states presented or if he can not decide between the two.

In practice, this step corresponds to the assessment given by the subject during, for example, a duochrome test. During this test, the subject is presented with an image comprising optotypes displayed on a red background on one side and optotypes displayed on a green background on the other side. If the subject has a better vision of the optotypes on the red background, the sphere should be decreased, and if he has a better vision of the optotypes shown on the green background, the sphere should be increased.

As a variant, for each current lens placed in front of his eye, the subject is asked to assess the quality of his vision through the current lens as compared to the previous lens: he is asked if the current lens provides a better vision or a worse vision than the previous lens or if he can not decide between the two. In this last case, the two lenses provide a similar vision quality for the subject.

The answers of the subject may be collected by different means, for example tactile means, oral means, thanks to a mouse, a ball mouse, a track pad, a continuous potentiometer . . . . These means may be put in action by the subject himself or by the eye care professional.

The value of the specific sensitivity parameter corresponding to this optical feature of the lens is representative of the smallest difference in said specific optical feature for which the subject may perceive a difference in the quality of the image seen while looking with said eye through lenses with different values of the specific optical feature.

Figure 2:
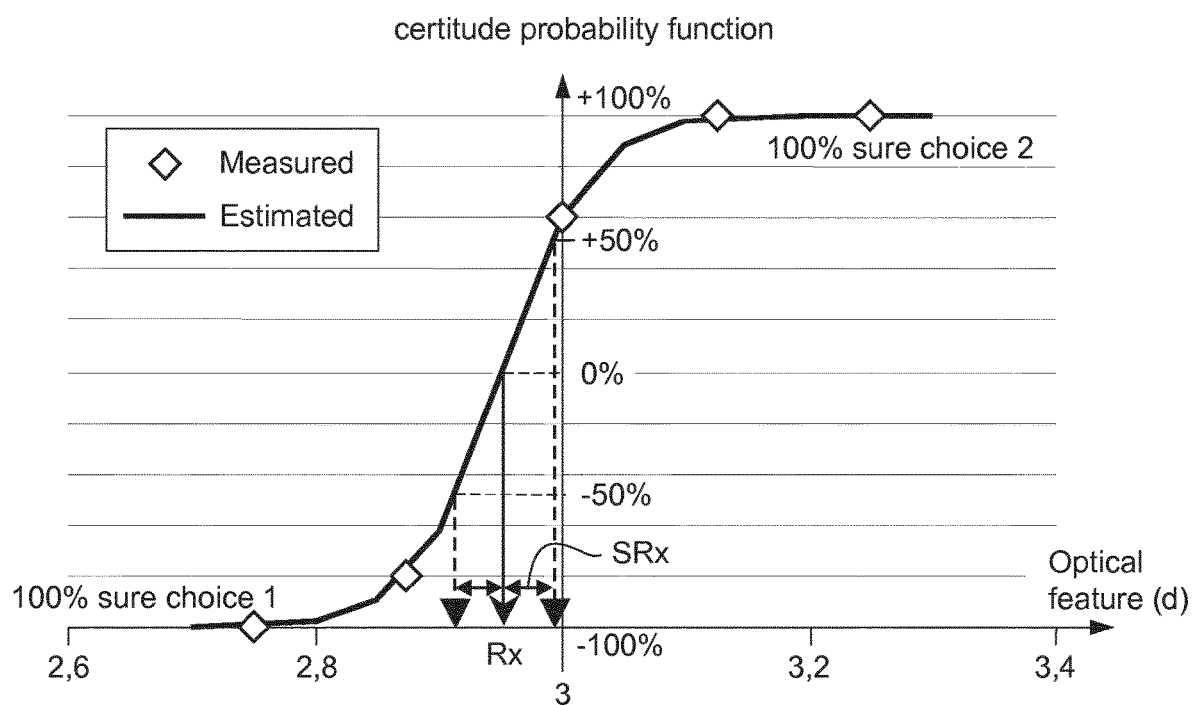
FIG. 2 is a graph of the subject's certitude probability function against the value of the optical feature that is used to determine the single value of a specific sensitivity parameter.

As shown on FIG. 2, the single value of the specific sensitivity parameter SRx may be determined, for example, as the width of half of the zone of the optical feature variation, for which the subject is insensitive to the change in the value of the optical feature of the lens placed in front of his eye. This zone corresponds to the range of values of the optical feature that could be acceptable for the subject or for which the subject cannot decide which lens provides a better vision.

The value of each specific sensitivity parameter is for example evaluated with a probability function of certitude of the subject's answers.

An example of the subject's certitude probability function or certitude function is shown on FIG. 2 as the graph of the certitude of the choice made by the subject as a function of the optical feature value of the lens placed in front of the eye (see FIG. 2).

The certitude probability function reflects the certainty of the subject when making a choice between the two visual states (for example vision on red or green background) or between two different lenses placed successively in front of his eye.

The 0% certitude value is the value obtained when the subject is unable to choose between the two visual states or the two lenses, that is to say, when the subject is unable to perceive any difference in the quality of the image seen in each visual state (red or green background for example) or the image seen through each of the two lenses. The −100% certitude value is the value obtained when the subject is certain that a first of the two visual state (for example optotypes on red background) provides a better quality of the image seen, or that the first lens provides a better quality of the image seen, and the 100% certitude value is the value obtained when the subject is certain that the second visual state (for example optotypes on green background) or second lens provides a better quality of the image seen.

The example of FIG. 2 shows the certitude probability function determined as a function of the optical feature in diopter, for example the sphere, of the lens placed in front of one of the eye of the subject.

Methods for determining the certitude probability functions are known from document WO2018/015381.

In practice, the better quality of the image may be assessed by the subject of the basis of:
the optotypes being seen sharper for evaluation of lenses with different sphere, cylinder or axis, for example in a Jackson Cross Cylinder procedure,
color better seen between red or green for a duochrome test,
vertical or horizontal directions of the image being sharper for a Jackson Cross test with fixed Jackson cross cylinders,
top or bottom position for binocular balance.

In this last case, vision of each eye is dissociated thanks to polarizer or prism or any other known means such that one eye sees the top part of the image (for example top line letters) and the other eye sees the bottom part of the image. The wearer is then allowed to compare both parts (top and bottom) of the image to find the best balance between the two eyes, being the difference in sphere value between the two eyes.

The certain choices of the subject are taken into account with the values −1 and +1 answers, "don't know" and "the same" answers being null. Any uncertain answer may be represented by a value between 0 and 1 depending of the estimated or measured certitude. The certitude function is calculated by averaging all the answers estimated for a particular optical feature value. The certitude function is then interpolated to any non-estimated value.

An insensitive zone is defined, corresponding to the values of the optical feature of the lens of which probability of certitude is comprised in a predetermined range of incertitude. The extreme values of this predetermined range of incertitude may be comprised between 20% and 80% on one side and between −20 and −80% on the other side.

Examples of the range of incertitude are the ranges [−20%, 20%], [−30%, 30%], [−40%, 40%], [−50%, 50%], [−60%, 60%], [−70%, 70%] or [−80%, 80%].

The value of the specific sensitivity parameter of the subject is then defined to be equal to half of the insensitive zone size. The theoretical value Rx of the optical feature adapted to the subject may be any value of the optical feature included in the range of incertitude and in particular the one corresponding to the value of certainty 0%.

The optical features for which the specific sensitivity may be assessed with the method described before are for example:
the sphere, also named spherical power,
the cylinder, also named cylindrical power and/or the axis or a combination thereof,
the astigmatism, defined as a combination of cylinder and axis,
the addition, used for example for progressive lenses, bifocal lense or monofocal lenses for near vision,
the binocular sphere,
the binocular balance.

All of these optical features may be given in diopters. Conventional methods for determining these optical features are well known for the man skilled in the art. These conventional methods may be used, as well as improved methods according to the invention as described below.

The sphere corresponds to the refractive power of the lens given by the spherical component of the shape of the front and back faces of the lens, in diopters.

The cylinder corresponds to the refractive power of the lens given by the cylinder component of the shape of the front and back faces of the lens in diopter.

The axis corresponds to the orientation of the cylinder component of the shape of the lens.

The cylinder power and axis describe the cylinder component of an ophthalmic lens determined to compensate the astigmatism of an eye of the subject. Instead of being determined in the standard polar form with magnitude and orientation decomposition, the current invention uses a vector decomposition of the cylinder component, as described in the document PCT/EP2018/061207 of the Applicant.

Figure 15:
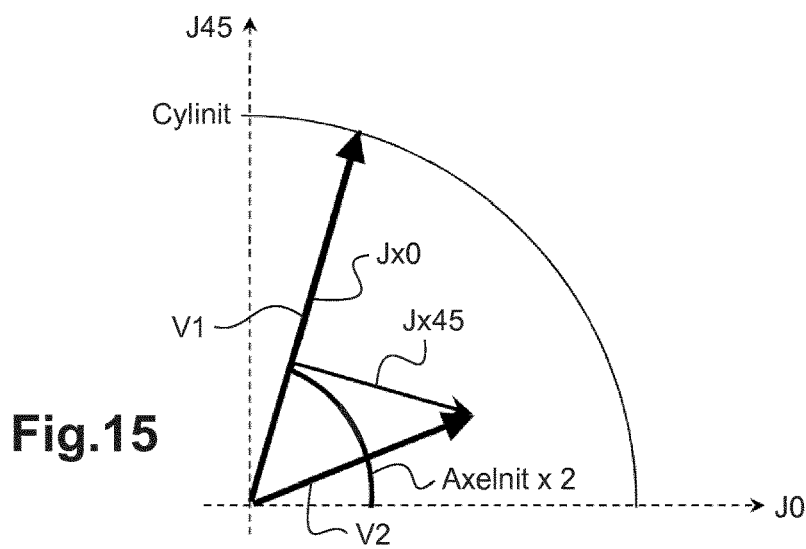
FIG. 15 shows the decomposition of the cylinder power and axis values of a lens in a J0, J45 vector base.

The vector decomposition of the cylinder component is done according to two orthogonal directions J0, J45 as shown for example on FIG. 15.

For example, the decomposition along the two J0, J45 directions corresponds to the replacement of the classical sphero-cylindrical notation (Sphere S, Cylinder C, axis) by a triplet of orthogonal values (S, J0, J45) defined as a spherical lens of power S and two Jackson crossed cylinder lenses one at axis 0° with a power $J0=(-C/2)*\cos(2*axis)$ and the other at axis 45° with a power $J45=(-C/2)*\sin(2*axis)$, as the astigmatism decomposition of the polar form of astigmatism (C, axis).

On FIG. 15, the initial cylinder component is represented by vector V1 in polar coordinates with the norm Cylinit and the angle equal to twice the axis 2× AxeInit.

Vector V2 is an example of a final correction tested.

To be closer to the standard Jackson crossed cylinder procedure, the two orthogonal directions may correspond to the initial astigmatism direction and its perpendicular direction as illustrated on FIG. 15. Each component of the decomposition is expressed in diopters, thus allowing defining and measuring two corresponding sensitivities. The component Jx0 determined along the initial astigmatism direction is associated to the cylinder power component and the perpendicular component Jx45 is associated to the axis component. In the following the cylinder and axis will refer to this definition.

The addition may be defined as the difference in sphere between far vision and near vision, for example between the far vision zone and the near vision zone of a progressive lens.

After determining the sphere and cylinder components of the correction needed by the subject, it is known that it may be needed to adjust the binocular balance of the eyes. To achieve a comfortable correction of the eyes of the subject, it is indeed useful to ensure that the quality of the images seen through the adapted lenses with the adapted sphere determined is similar.

The determination of the value of the adapted sphere of the lens for each eye of the subject may indeed not be performed as accurately for both eyes. It is then useful to compare the quality of the images seen by each eye with the corresponding adapted lens having the adapted sphere, thanks to known methods allowing dissociation of the images seen by each eye, such as using two polarizers oriented at 90°, one of these polarizers being placed in front of each eye. If one of the adapted lenses determined provides a better image than the other, the sphere of this lens may be modified in order to make the quality of the images seen by the subject similar.

The corresponding optical feature may then be equal to the difference between the sphere of both lenses.

It may also be equal to the difference between the interval between the sphere of both lenses initially determined before the binocular balance test and the interval between the sphere of both lenses after the binocular balance test.

A certitude function may be determined as a function of one or the other of these optical features. An insensitive zone may be identified and the value of the specific sensitivity parameter of the subject to the binocular balance adjustment may be determined in a way similar to what was described before.

After adjusting the binocular balance, the binocular sphere may be adjusted. Based on the values of sphere determined previously, for example after the binocular balance test, the sphere of both lenses are varied simultaneously with the same increment, and the quality of the binocular vision is assessed by the subject. The subject is then asked to compare the quality of the image seen when varying both sphere.

The corresponding optical feature of each lens or of the couple of lenses may then be equal to the difference between the sphere initially determined before the binocular sphere test and after the binocular sphere test. The corresponding sensitivity parameter is relative to the sensitivity of the subject to this adjustment.

A certitude function may be determined as a function of this optical feature. An insensitive zone may be identified and the value of the specific sensitivity parameter of the subject to the binocular sphere adjustment may be determined in a way similar to what was described before.

Different single values of said at least a first and second sensitivity parameters may be determined in step a) and b) with different measuring methods.

Different single values of said at least a first and second sensitivity parameters may also be determined in step a) and b) in similar or different measurement conditions.

For example, single values of the first and/or second sensitivity parameter may be determined at different visual distances or for the same visual distances.

The single values of the specific sensitivity parameter may therefore be relative to the sensitivity of the subject to said first and/or second optical feature of one lens or a couple of lens in conditions of far vision, intermediate vision or near vision. It may also be relative to specific measurement conditions, such as the ergonomics of the phoropter: pantoscopic angle, wrap angle of the phoropter.

Single values of the first and/or second sensitivity parameter may be determined with different light conditions.

The single values of the specific sensitivity parameter may therefore be relative to the sensitivity of the subject to said first and/or second optical feature of one lens or a couple of lens in conditions of daylight vision, weak light vision or night vision.

Other environmental conditions having an impact on the visual performances of the subject may also be taken into account.

Step c)

In step c), said combination of said single values of the first and second sensitivity parameters comprises generally a linear combination or a non-linear combination, for example a quadratic combination, of some or all of the single values of the first and second sensitivity parameters.

The global sensitivity parameter is for example an averaged value of several single values of specific sensitivity parameters. It may be a weighted averaged value of several single values of specific sensitivity parameters.

In an embodiment, in step c), said combination of said single values of the first and second sensitivity parameters comprises a mean value of the single values of the first and second sensitivity parameter determined during steps a) and b).

For example, several single values of the same specific sensitivity parameter, that is to say, relative to the same eye or couple of eyes and to the same optical feature of a lens or couple of lenses are determined in the same environmental conditions and the mean of these single values is determined.

In an embodiment, such global sensitivity parameters are for example:
  a mean sphere sensitivity of the right or left eye SmphOD, SmsphOG obtained by averaging several single values SphOD, SphOG of the sphere sensitivity parameter for the right or left eye,
  a mean binocular sphere sensitivity Smsphbino, a mean cylinder sensitivity of the right or left eye SmcylOD, SmcylOG obtained by averaging several single values ScylOD, ScylOG of the sphere sensitivity parameter for the right or left eye,
  a mean axis sensitivity of the right or left eye SmaxisOD, SmaxisOG obtained by averaging several single values SaxisOD, SaxisOG of the sphere sensitivity parameter for the right or left eye, or
  a mean sensitivity of the eyes to binocular balance Smeqbino.

These mean values are averaged in order to be more reliable than the single values.

In another embodiment, the single values of the first and second sensitivity parameters determined during step a) and b) are either:
  single values of the cylinder sensitivities ScylOD, ScylOG of each of the left and right eyes
  or
  single values the axis sensitivities SaxisOD, SaxisOG of each of the left and right eyes,
  or single values of the sphere, cylinder, axis and binocular balance sensitivities SsphOD, ScylOD, SaxisOD, SsphOG, ScylOg, SaxisOG, Seqbino of one of the left and right eyes,
and, in step c), the value of the global sensitivity parameter determined is respectively
  the value of a global cylinder sensitivity parameter (Sgcyl) equal to the mean value of the single values of the cylinder sensitivities of the left and right eyes: Sgcyl=(ScylOD+ScylOG)/2
  or
  the value of a global axis sensitivity parameter (Sgaxis) equal to a mean value of the single values of the axis sensitivities of the left and right eyes: Sgaxis=(SaxisOD+SaxisOG)/2
  or
  the value of a global left or right eye sensitivity parameter (SgOG, SgOD) equal to the mean value of the single values of the sphere, cylinder, axis and binocular balance sensitivities of only the left or only the right eye:

SgOG=SsphOG+ScylOG+SaxisOG+Seqbino)/4

SgOD=SsphOD+ScylOD+SaxisOD+Seqbino)/4.

These global sensitivity parameters are specifically relative to one of the eyes of the subject. They are especially useful, for example, in the case where the sensitivities of each eye are very different, for example in case the needed correction for each eye or visual performance (visual acuity) is very different, or dominance of one eye is significative.

Alternatively, during step a) and b), single values of the sphere sensitivity of each of the left and right eyes SsphOG, SsphOD of the subject and a single value of the sphere binocular sensitivity (Sphbino) of said subject are determined, and,
  in step c), the value of the global sensitivity parameter determined is the value of a global sphere sensitivity parameter Sgsph is equal to a mean value of the single values of the sphere sensitivities of the left and right eyes SsphOG, SsphOD and of the sphere binocular sensitivity Ssphbino: Sgsph=(SsphOG+SsphOG+Ssphbino)/3.

The sphere is usually the parameter for which subjects are most sensitive. In the other hand, it may be more fluctuating due to accommodation fluctuation. Therefore, the determination of the value of a global sphere sensitivity parameter such as this one may be advantageous to evaluate the sensitivity of the subject to the sphere.

An overall sensitivity taking into account all of the above described sensitivities and the mean sensitivity of the eyes to binocular balance Sgeqbino may be defined as equal to the mean value of the global sphere sensitivity Sgsph, the global cylinder sensitivity Sgcyl, the global axis sensitivity Sgaxis and the mean sensitivity of the eyes to binocular balance Sgeqbino:

Soverall=(Sgsph+Sgcyl+Sgaxis+Sgeqbio)/4.

The values obtained for the right and left eyes and for the main optical features of the lenses are averaged.

Other similar global sensitivity parameters taking into account the sensitivity of each eye may be determined as:
  another global sphere sensitivity equal to the mean value of the mean sphere sensitivity of the right or left eye SmsphOD, SmsphOG, and the mean binocular sphere sensitivity Smsphbino;
  another global cylinder sensitivity equal to the mean value of the mean cylinder sensitivity of the right or left eye SmcylOD, SmcylOG;

another global axis sensitivity equal to the mean value of the mean axis sensitivity of the right or left eye SmaxisOD.

The overall sensitivity may also of course be calculated directly on the basis of the single values of the specific parameter, without calculating intermediate mean values, or on the basis of averaged values of the single values:

$$Soverall=[(SsphOD+SsphOG+Ssphbino)/3+(ScylOD+ScylOG)/2+(SaxisOD+SaxisOG)/2+Seqbino]/4 \text{ or}$$

$$Smoverall=[(SmsphOD+SmsphOG+Smsphbino)/3+(SmcylOD+SmcylOG)/2+(SmaxisOD+SmaxisOG)/2+Smeqbino]/4.$$

Another global sensitivity parameter to astigmatism Sgasr taking into account cylinder and axis may be defined as Sgasr=(Sgcyl+Sgaxe)/2.

With the definition of cylinder and axis in diopter, these optical features could be noted J0 or Jx0 and J45 or Jx45 and Sgasr could be expressed as the mean value of the single value of the sensitivity to components J0 or Jx0 and J45 or Jx45 of the cylinder or the mean value of the averaged sensitivity to J0 or Jx0 and J45 or Jx45: Sgasr=(SJ0+SJ45)/2 or Sgasr=(SJx0+SJx45)/2 or Sgasr=(SmJ0+SmJ45)/2.

The value of a global cylinder component J0 and J45 or Jx0 and Jx45 sensitivity parameter SgJ0, SgJ45 or SgJx0, SgJx45 equal to the mean value of the single values of the cylinder component J0 and J45 or Jx0 and Jx45 sensitivities of the left and right eyes may also be defined: SgJ0=(SJ0OD+SJ0OG)/2 and SgJ45=(SJ45OD+SJ45OG)/2 or SgJx0=(SJx0OD+SJx0OG)/2 and SgJx45=(SJx45OD+SJx45OG)/2.

Corresponding global sensitivities may of course be determined with any base vector J0, J45; Jx0, Jx45 as described before.

An overall sensitivity may also be defined for the right eye SgOD or left eye SgOG only:

$$SgOD=(SgsphOD+SgcylOD+SgaxisOD+SgeqbioOD)/4,$$

$$SgOG=(SgsphOG+SgcylOG+SgaxisOG+SgeqbioOG)/4.$$

Tests based on the value of the overall sensitivity parameter showed that more sensitive subjects choose more often the more precise lens than all the population and better see benefits and differences.

Tests also showed that the more sensitive are the subjects, the less "no choice" they made and the more they choose the more precise lens, that is the higher they perceive a benefit of the precision, thus validating the reliability of the overall sensitivity parameter.

The global sensitivity parameter, in particular the overall sensitivity parameter may also be representative of sensitivity to aniseikonia, that is to a difference retinal image size.

The determination of the value of the global sensitivity parameter may also comprise:
  an estimation of the sensitivity to aniseikonia,
  a subjective and/or objective determination of the sensitivity to sphere, and/or cylinder, and/or axis, and/or addition, and/or binocular sphere and/or binocular balance for example taking into account accommodation,
  a comparison based on realistic scenes.

In another embodiment, in step c), said combination of said single values of the first and second sensitivity parameters comprises a weighted mean value of the single values of the first and second sensitivity parameter determined during steps a) and b).

The weights associated to the single values of the first and second sensitivity parameters may for example depend on:
  a usual visual behavior of the subject, and/or
  a type of lens to be worn by the subject, and/or
  activities that the subject wishes to have with the lens, and/or
  an eye dominance data, and/or
  an assessment of the comfort of a current/previous lens worn by the subject, and/or
  data indicated on the previous prescription for an optical correction equipment.

This is schematically represented on FIG. 1 by blocks 130, 140 and 150.

The weights that are taken into account are for example higher for the single values of the specific sensitivity parameters relative to the dominant eye of the subject than the weights associated to the single values of the specific sensitivity parameters relative to the non dominant eye of the subject.

Other usual behavior of the subject to take into account may for example comprise the following: eye-head coordination, eye-hand or eye-foot coordination, hand or foot dominance (preference), walking behavior, eye mover/head mover behavior.

In a variant, or additionally, said weights are higher for the single values of the cylinder sensitivity of each eye than the weights associated to the single values of the sphere sensitivity of each eye if the subject is a progressive lens subject.

Weights may also be associated to activities usually done by the subject, for example: reading, using a smartphone or a tablet or a computer, watching TV, driving, practicing some sports, having static activities, dynamic activities or moving . . . .

Reading, using a smartphone or a tablet will imply the use of a higher weight for sensitivity parameters determined in near vision, using a computer or watching TV will imply the use a higher weight for sensitivity parameters determined in intermediate vision.

The weights taken into account for determining the global sensitivity parameter may for example also be higher for optical features of the lens for which the subject report to have had adaptation problems on the previous ophthalmic equipment. For example, complaints about distortion or visual field being not wide enough may be taken into account.

For example, a higher weight may be used for addition or near vision sensitivity if the subject complains about near vision, a higher weight may be used for cylinder sensitivity if the subject complains about distortion, a higher weight may be used for the dioptric parameter with the largest change in the new equipment if the subject complains about adaptation to the previous equipment.

The combination weights can alternatively be determined based on an acuity model.

For example, according to the acuity model of Le Grand, the ratio between the refraction error linked to the astigmatism of the eye and the refraction error linked to the sphere equal to $\sqrt{2}/2$, as published in *Le Grand Y.: "Sur le calcul des verres de lunetterie", Revue d'Optique, Paris,* (1966).

A global sensitivity parameter could therefore be defined as:

$$Swoverall\_1=(Sgsph+2/2Sgcyl)/2 \text{ or } Swoverall\_2=(Sgsph+v2/2Sgasr)/2$$

with the previously defined notations.

According to another example, data acquired by Sloan and published by Sloan L. L. in *Measurement of visual*

*acuity. Arch. Ophtalmol.* 45, (6), 704-725, (1951) indicate that the ratio between the refraction error linked to the astigmatism of the eye and the refraction error linked to the sphere is equal to 0.8 for visual acuities over 20/28.

A global sensitivity parameter could therefore be defined as:

Swoverall_3=(Sgsph+0,8Sgcyl)/2 or Swoverall_4= (Sgsph+0,8Sgasr)/2 with the previously defined notations Sgsph and Sgasr.

According to yet another example, the decrease of the relative acuity VA %, that is to say of the acuity of the subject with a spherical error DPPO and an astigmatic residual error ASR, as compared to the acuity of the subject with a perfectly corrected eye, in a non presbyopic subject, may be determined as:

VA %=100-63.DPPO-44,3.ASR+7,2.DPPO$^2$+19, 5.DPPO.ASR+ASR$^2$.

This formula may be used if the DPPO is positive or equal to zero.

In this formula, the magnitudes DPPO and ASR quantify the optical effect of the difference between the eye of the subject and a perfect eye. The magnitude DPPO and ASR therefore correspond to the values of the sphere, cylinder and axis of the adapted corrective lens for the subject.

This formula could be extended to presbyopic patient by determining the remaining subjective accommodation as a function of age and an ergorama, as described in FAUQUIER C., BONNIN T., MIEGE C., ROLAND E.: *"Influence of Combined Power Error and Astigmatism on Visual Acuity"*. *Ophthalmic and Visual Optics Technical Digest*, (*Optical Society of America,* Washington, D.C.), Vol. 1, p. 151-154, 1995.

The corresponding global sensitivity parameter could be calculated as:

Swoverall_5=63*Sgsph+44.3*Sgasr-7.2*Sgsph$^2$– 19.5*Sgsph*Sgasr-Sgasr$^2$.

In a general manner, if a criteria for evaluating a monocular visual performance P is calculated as: P=m. DPPO$^a$+ n.ASR$^b$, with m, n>=0 and a and b comprised between 0 and 2, a global sensitivity parameter Swoverall_i may be evaluated as Swoverall_i=m.Sgsph$^a$+n.Sgasr$^b$, with Sgsph and Sgasr the global sensitivity parameters as described before.

Visual acuity models are known from various document, for example from: *"Unaided Visual Acuity and Blur: A Simple Model"* by Ralf Blendowske, or *"Phenomenological model of visual acuity"* by José A. Gómez-Pedrero.

More specifically, it is here proposed to take into account a specific visual acuity model developed by the Applicant. According to this model, the visual acuity follows Swaine's law for very small values of errors DPPO and/or ASR, for example for DPPO or ASR smaller than 0.5 D, it follows Gomez' law for small errors of DPPO an/or ASR, comprised for example between 0.5 and 1.75 D, and it follows Blendoswke's law for higher level of errors.

The invention also relates to a system for determining said value of a global sensitivity parameter Sgsph, Sgcyl, Sgaxis, Sgasr, SgJ0, SgJ45, Soverall of a subject, comprising:

means for determining a single value of at least a first sensitivity parameter of said subject, relative to the sensitivity of the subject to a variation of a first optical feature of at least a first ophthalmic lens, means for determining a single value of at least a second sensitivity parameter of said subject, relative to the sensitivity of the subject to a variation of a second optical feature of at least a second ophthalmic lens, computing means programmed for determining said value of the global sensitivity parameter taking into account a combination of said single values of the first and second sensitivity parameters.

The means for determining said single values of the first and second sensitivity parameter may be the same or different means. These means comprise for example a phoropter as described before coupled to analysis means programmed to analyze the answers of the subject to the test protocol described before. This analysis means may be integrated to the phoropter or may be independent analysis means. In this last case, the analysis means comprise a communication module adapted to receive data from the phoropter.

The means for determining a single value of at least a first sensitivity parameter of said subject may also comprise inputting means to input the single value retrieved from a previous test. It may also comprise communication means adapted to receive said value.

This system may further comprise means for storing said value of the global sensitivity parameter determined by the computing means, and/or means for displaying said value of the global sensitivity parameter determined by the computing means.

The means for storing said value may comprise a memory or a local or distant server. The means for displaying may comprise a screen or any kind of display integrated or not to the phoropter.

The value of the global sensitivity parameter of the subject thus determined, with any of the possible formula and methods mentioned before, may be taken into account at many different steps of the process of providing an corrective equipment adapted to improve the vision of the subject.

The value of the global sensitivity parameter determined gives indeed reliable information on the perception of the subject to differences between two different pieces of equipment. It may then help the subject and the eye care practitioner to decide on the features of the corrective equipment most adapted to the subject at the better cost.

It will be indeed useless to determine the refraction or provide a lens with an accuracy that is higher than the global sensitivity of the subject, as the subject will not be able to distinguish any difference between lenses with dioptric differences smaller than the value of the global sensitivity parameter.

The invention therefore also relates to a method for informing an eye care practitioner of the value of a global sensitivity parameter of a subject, said global sensitivity parameter being relative to the sensitivity of said subject to a variation of at least an optical feature of at least an ophthalmic lens place in front of at least one eye of said subject, comprising the following steps:

determining at least a value of a global sensitivity parameter of a subject according to any of the methods described above, displaying this value of the global sensitivity parameter for informing said eye care practitioner Such a method may also help the eye care practitioner to optimize the test protocol for determining the refraction of the other eye.

It may also help the eye care practitioner to recommend a frame based on the value of the pantoscopic and wrap angle . . . .

The eye car practitioner may then take into account the value of the global sensitivity parameter for determining the refraction, as explained below, and/or for prescribing the appropriate lenses.

Different kind of display may be considered for the global sensitivity parameter.

The global sensitivity may be displayed as a sight size on a target and used to evaluate the matching between the exact refraction of the subject and the final correction of the lens provided to the subject.

Examples of such targets 10, 20 are shown on FIG. 3. The bigger target 10 represents the value of the global sensitivity of a first subject, and the smaller target 20 represents the value of the global sensitivity of a second subject, more sensitive than the first subject. On this example of display, the abscissa is the sphere and ordinate is the cylinder, the center of the target is placed at the values (S1, C1), (S2, C2) of the refraction determined for one of the eyes of the subject and the inner ring 11, 21 of the target 10, 20 is placed in order to be spaced from the center 12, 22 of the target by the value of the global sensitivity parameter of the subject.

As a variant, the abscissa and ordinate could give the values of any of the optical features for which sensitivity of the subject may be determined.

The shape of the inner ring of the target could also be different. In the example shown, the value of the global sensitivity parameter takes into account both sphere and cylinder and is therefore the same on abscissa and ordinate.

The target could also take into account the values of two different global sensitivity parameters, for example a global sensitivity in sphere and a global sensitivity in cylinder. In this case, if the subject has different sensitivities to sphere and to cylinder, instead of a circular ring, elliptical rings could be used.

The zone of the target located inside the inner ring therefore gives the range of possible values of the optical features of the lens plotted in abscissa and ordinate for which the subject will perceive a perfect visual correction.

It is possible to use this display to superimpose the target representing the global sensitivity of the subject with a sign 30, 40, 50, 60 representing the value and accuracy of the corresponding optical features of the lens actually provided to the subject on the basis of the refraction determined with usual refraction methods.

The sign 30, 40, 50, 60 is placed on the display with the same conventions for abscissa and ordinate. A central region 31, 41, 51, 61 of the sign 30, 40, 50, 60 is centered at the coordinates corresponding to the optical features of the lens and the size of this central region 31, 41, 51, 61 corresponds to the accuracy of the value of the optical feature of the lens.

This allows calculating a matching score related to the probability of the lens provided to the subject to have optical features located in the zone inside the inner ring 11, 21 of the target 10, 20, and therefore to the probability of providing an equipment with which the subject will perceive a perfect visual correction.

This is done for example by calculating the area of the inner ring of the target covered by the central region of said sign.

On the examples of FIGS. 4 and 5, the sign 30, 40, 50, 60 is a central disc 31, 41, 51, 61 with radial branches 32, 42, 52, 62. The matching score is calculated as a function of the area of the zone inside the inner ring 11, 21 of the target 10, 20 covered by the central disc 31, 41, 51, 61 of the sign 30, 40, 50, 60.

The example of FIG. 4 shows the case where the refraction of the subject is determined with low accuracy, and therefore, the lens provided based on this determination has also a low accuracy. This is for example the case of a refraction determined with 0.25 diopter accuracy.

In this case, 95% of the central disc 31 of the sign 30 is located inside the inner ring 11 of the target 10, which means that for a first subject with a low global sensitivity corresponding to the bigger target 10, the probability to obtain a value of refraction and therefore a lens able to provide a perfect visual correction of this first subject is 95%. On the contrary, only 15% of the central disc 41 of the sign 40 is located inside the inner ring 21 of the smaller target 20, which means that for a second subject with a high global sensitivity corresponding to the smaller target 20, the probability to obtain a value of refraction and therefore a lens able to provide a perfect visual correction of this first subject is 15%.

The example of FIG. 5 shows the case where the refraction of the subject is determined with high accuracy, and therefore, the lens provided based on this determination has also a high accuracy. This is for example the case of a refraction determined with 0.01 diopter accuracy.

In this case, 100% of the central disc 51, 61 of the sign 50, 60 is located inside the inner ring 11, 21 of the target 10, 20 which means that for both first and second subjects, the probability to obtain a value of refraction and therefore a lens able to provide a perfect visual correction for these first and second subject is 100%.

Of course, many other shapes could be used for schematically representing the target and/or the sign.

Currently, mainly visual acuity is taken into account to assess if a lens has an effective effect for improving the vision of the subject, and to predict if the subject will be comfortable with its prescription. When it comes to the eye care practitioner to decide whether to favor or penalize an eye at the time of prescription, his/her decision is mainly based on visual acuity.

Now, with the calculation of the value of the global sensitivity parameter of the subject, the eye care practitioner may be informed of this value, which may help the eye car practitioner to decide which eye should be privileged when determining and prescribing the lenses. The value of the global sensitivity parameter of the dominant eye, or of the eye with highest sensitivity may in particular be taken into account.

Until now only the measure of visual acuity was used to help the eye care practitioner to take a decision about which eye should be privileged. Sometimes the visual acuity is similar in both eyes, for example in case of little variations of prescription and the adaptation of the subject to his new equipment can be difficult and longer.

Now, eye care practitioner may take care to prescribe a limited change in the prescription of the most sensitive eye, particularly if it corresponds to the dominant eye or otherwise clearly warn his/her patient of a possible longer period of adaptation.

The value(s) of the global sensitivity parameter(s) of the subject may be taken into account to determine the appropriate accuracy of the refraction to measure and/or of the lens to prescribe to this subject.

A method for prescribing a lens for improving the vision of a subject could indeed comprise a step of determining the value of a global sensitivity parameter as described before, and a step of prescribing the lens adapted to the subject while taking into account this value.

In the second step, lenses would be prescribed with accuracy similar to the value of the value of the global sensitivity parameter.

Prescribing values with accuracy higher than the value of the global sensitivity parameter is indeed useless. Prescribing values with accuracy lower than the value of the global sensitivity parameter may lead to unsatisfactory results.

Changes in the previous prescription should not be done if they are smaller than the value of the global sensitivity parameter. On the contrary, any change above the value of the global sensitivity parameter should be done.

However, the eye care practitioner should avoid very high changes (typically above 3 to 5 times the sensitivity) when sensitivity is high due to possible adaptation difficulties.

The information relative to the value of the global sensitivity parameter may therefore help the eye care practitioner with the prescription.

The value of the global sensitivity parameter may also be used during the refraction to adjust the refraction process accordingly in real time, as discussed later.

Regarding the display of values of different global sensitivity parameters, they may be displayed in a sensitivity map.

The sensitivity map of the subject is adapted to provide help for prescribing the lens and/or take it into account to suggest or modify a lens optical design.

The sensitivity map of the subject may easily be compared to a reference sensitivity map.

On FIG. 6, for example, the sensitivity map 2 of the subject is compared to a reference sensitivity map 1. The reference sensitivity map 1 is for example a sensitivity map obtained by averaging the values of the global sensitivity parameters determined for each individual of a given population.

As already mentioned, the value of the global sensitivity parameter of the subject may be taken into account during the determination of the refraction of the eyes of this subject.

As described before, the value of the global sensitivity parameter is determined during the steps usually performed for determining the refraction of the eyes of the subject. It may then either be taken into account in real time during this determination or during an ulterior determination of the refraction.

The invention thus also relates to a method for determining an adapted optical feature of an ophthalmic lens adapted to improve the vision of a subject, comprising the following steps:

performing a test protocol comprising repeated steps of:
placing a test lens in front of an eye of the subject,
assessing the quality of vision of the subject looking through said test lens,
the value of the optical feature of the lens being incremented by a incremental value between each repetition of said steps,
comparing the quality of vision of the subject looking through at least two successive lenses placed in front of the eye of the subject during two successive repetition of said steps of the test protocol, and determining said adapted optical feature based on this comparison,
determining at least a value of a global sensitivity parameter of a subject according to the method described above,
determining said incremental value taking into account this value of the global sensitivity parameter.

Said test protocol is a standard procedure as well known from the man skilled in the art, performed for example by using a phoropter.

Different types of phoropter may be used. In particular, a phoropter using lenses with variable optical features, such as a lens with a variable sphere power as described in documents US20160331226 and US2017027435. A classical phoropter using multiple lenses of different powers may also be used.

The test protocol usually starts with a predetermined value of the optical feature, for example the optical feature of the previous visual correction equipment or an objective value determined with an autorefractometer.

Said step of determining the value of the global sensitivity parameter may either be performed during the same test protocol, or during a test protocol performed before.

In the first case, the test protocol may initially be performed with a standard incremental value while the value of the global sensitivity parameter is determined, and the steps of the test protocol may be repeated once again with the incremental value determined in order to determine the refraction of the eyes of the subject. The incremental value is then adjusted in real time.

In the second case, the value of the global sensitivity parameter is saved in a memory in association with the data of the subject, and it is used later to determine the incremental value before performing the test protocol.

More precisely, said incremental value is determined to minimize the difference between this incremental value and the value of the global sensitivity parameter.

This allows determining an accurate value of the refraction, sufficiently accurate to ensure determining a lens that will provide a correction as good as possible for the subject, close to perfect vision. It also avoids determining the refraction with accuracy uselessly high, as accuracy higher than the value of the global sensitivity parameter will lead to no further improvement of the vision, but may have practical drawbacks, such as being longer to determine for the subject.

The accuracy is here defined as the difference between the value of the refraction determined through the method and the actual current refraction of the eyes of the subject.

During usual test protocol for determining the dioptric features of the lens adapted to correct the visual defects of the eye of the subject, one of the dioptric features of the test lens is decreased or increased step by step. The starting point is often the dioptric feature of the previous equipment of the subject, if any, or an objective measurement of an autorefractometer.

As described before in relation with the determination of the value of the global sensitivity parameter, for the lens with the current optical features placed in front of his eye, the subject is asked to assess the quality of his vision through the current lens as compared to the previous lens: he is asked to express a visual assessment that corresponds to an indication of a preferred visual state among two visual states presented or if he can not decide between the two.

In practice, this step corresponds to the assessment given by the subject during a duochrome test or when comparing two different lenses.

The subject then indicates his answer, for example "better vision on red background" or "better vision on green background" or "better vision with first lens or with second lens".

In case of "I don't know" answer, that is, in case of answers where the subject may not choose between the two visual states or the two lenses, the usual protocol is to skip this step and go on with the test protocol by presenting another duochrome test with another optical feature of the lens or another optotype reading with another lens.

Usually, the sphere, cylinder or axis is changed when going to the next step in the same way as before, that is by increasing the sphere, cylinder or axis of the lens when it was increased before or decreasing the sphere, cylinder or axis of the lens when it was decreased before.

However, it may be useful to test new values from both sides and/or start from a predetermined side of the one currently tested, in order to control accommodation of the subject.

When testing the far distance vision, it is indeed important to try to minimize accommodation of the subject during the test.

When testing the sphere needed by the eye of the subject, it is then useful to test a new value of the sphere that is more positive than the value giving rise to the "I don't' know" answer, since this answer might signify that the current value of the sphere is close to be adequate or that the subject is accommodating.

If the subject believes his vision is worse with this more positive value of the sphere, the adequate value of the sphere is in between (so the next value of the sphere is decreased). If the subject gives another "I don't know" answer or believes his vision is better, the test protocol goes on by increasing the sphere.

When testing other optical features such as cylinder and axis, new values of the optical feature that frame the value giving rise to the "I don't' know" answer are tested. This is especially the case when the "I don't know" answer is the first answer given when starting the test.

When testing the near vision of the subject, accommodation is maximized. The process is mirrored from that for distance vision. When testing the sphere, a more negative value is tested after the "I don't know" answer. The sphere to test in then decreased until answer is no more "I don't know". Then the value of the sphere is finally increased.

A similar process is applied for cylinder or axis, especially for first answers being "I don't know".

The test protocol for determining an adapted optical feature of the lens for the subject may also be customized depending on the subject and/or according to the habits or wishes of the eye care professional performing it.

For example, the test protocol is customized as a function of the historical data available for the subject, for example as a function of the value of his global sensitivity parameter, his visual defect (myopia . . . ), as a function of the optical features of his current equipment or as a function of his age. For children, no test in conditions of near vision is for example performed.

The invention also relates to a method for selecting an appropriate optical design for an ophthalmic lens adapted to improve the vision of a subject, among a list of predetermined optical designs, said optical design comprising the current values of at least one optical feature of the corresponding lens associated with a plurality of gaze directions of the subject when the lens is worn by said subject by taking into account the value of at least one global sensitivity parameter.

Said list of predetermined optical design comprises different optical designs, for example different power layout or astigmatism layout or acuity layout as a function of the subject's gaze direction in wearing conditions, all adapted to the visual correction needed for the subject, for example adapted to the refraction of the subject.

A predetermined optical design is selected among said list of predetermined optical in order to minimize the gap between at least one optical feature of the lens having this selected predetermined optical design and a target optical feature determined taking into account the sensitivity of the subject to this optical feature or to a different optical feature.

This method comprises here the following steps:

determining at least a value of a global sensitivity parameter of a subject according to the method described above, determining an adapted value of at least said optical feature adapted to improve the vision of the subject, determining, for several gaze directions of said lens having said predetermined optical design, the difference between the current value of the optical feature of the lens in each of said gaze direction and the adapted value of said optical feature, comparing this difference with the value of the global sensitivity parameter of the subject, selecting, among said list of predetermined optical designs, the appropriate optical design taking into account this comparison.

The optical design of the lens designates a set of parameter allowing defining a optical function of the lens. It therefore comprises a set of data associating a gaze direction of the subject through the lens and the value of an optical feature of the lens at the intersection between this gaze direction and the lens. The optical design comprises in particular a set of data associating each gaze direction to the value of a dioptric feature of the lens. It then provides the effect of the lens on light rays passing through the lens for each gaze direction.

The gaze direction of the subject is measured compared to a reference gaze direction that corresponds to the gaze direction of the subject going through a particular reference point of the lens, for example the optical center of the lens (for a unifocal lens) or the fitting cross of the lens (for a progressive power lens). It is determined by at least one, preferably two angles of the gaze direction compared to the reference gaze direction.

The predetermined optical design corresponds to a map of the optical features of the lens as a function of the gaze direction of the subject.

In practice, a region of the optical design for which said difference is smaller than the value of the global sensitivity parameter of the subject is determined. This region corresponds to a sub-set of gaze directions.

This region of the optical design corresponds to the zone of perfect vision of the corresponding lens, because the error on the optical feature arising in this region is not perceived by the subject.

In practice, the method for selecting the appropriate predetermined optical design comprises:

determining said region of said predetermined optical design for which said difference is smaller than the value of the global sensitivity parameter of the subject, selecting the appropriate optical design by selecting the optical design having the region with a larger size in at least one predetermined direction of the lens, and/or having a shape closer to a predetermined shape.

For example, this can be done by calculating the area of the region.

Preferably, the global sensitivity parameter considered is relative to the optical feature examined.

This selection does not include any modification of the predetermined optical design as listed. The method for selecting the optical design only allows to identify the predetermined optical design that will be most appropriate for the subject.

For example, the optical design with the largest region for which said difference is smaller than the value of the global sensitivity parameter of the subject, among all the optical designs of the list of optical designs, is selected. Alternatively, the optical designs having said region exhibiting a size larger than a predetermined size threshold value are selected.

Figure 7:
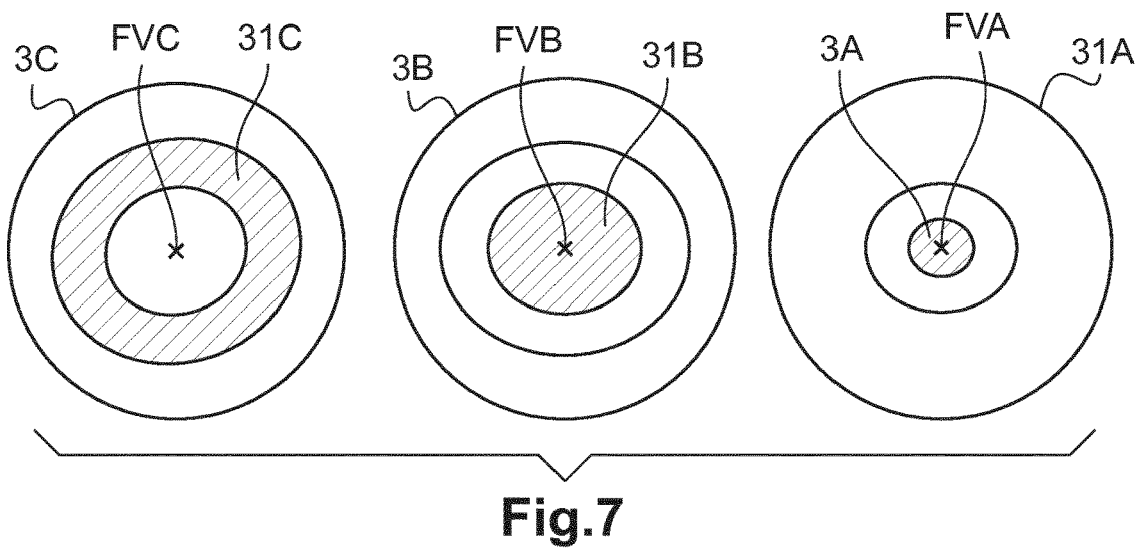
FIG. 7 is a schematic representation of three different standard predetermined optical designs for a lens.

FIG. 7 shows an example of a list of predetermined optical designs for a lens. These optical designs are represented by lines along which a given optical feature presents the same values. These lines correspond to the intersection of gaze direction with a mean surface of the lens, projected in a plane for 2D representation.

This given optical feature may for example be the sphere, cylinder or axis of the lenses, or a combination of sphere, cylinder and axis, for example representative of the visual acuity of the subject. For example, lines where the sphere of the lens will be the same are represented for three different designs on FIG. 7.

The region for which said difference is smaller than the value of the global sensitivity parameter of the subject, corresponding to the zone of perfect vision of each corresponding lens, is shown on this figure by a hatched zone. It is possible to show to the subject this graphical representation, representing the lens and the area of the lens that will provide a perfect vision in the corresponding lens.

In the case of predetermined optical designs 3A, 3B, the hatched zone 31A, 31B corresponds to the zone of perfect vision. It is center around the far vision gaze direction FVA, FVB of the optical design 3A, 3B.

In the case of optical design 3B, the hatched zone 31B is larger than the hatched zone of optical design 3A. This may be due to differences in many factors such as the pantoscopic parameter, wrap angle, aspherization of the lens. This optical design 3B will therefore be selected over the other optical design 3A.

In the case of optical design 3C, the area of perfect vision does not cover the far vision zone. This is an important drawback for this optical design. In certain case, the perfect vision area may not exist, because all gaze directions show a difference with the refraction higher than the subject's global sensitivity parameter's value.

The predetermined shape may be for example a target shape having a target dimension, for example a shape having a predetermined angular dimension in one direction, or may be for example an elongated shape in one predetermined direction.

It is also possible to provide instead or in addition a score of the perfect vision zone size, for example equal to the angular area of the corresponding lens providing perfect vision in square degrees.

It is also possible to provide different graphical representation of zones of interest and determine: said zone of perfect vision for which the difference defined before is smaller than the value of the global sensitivity parameter of the subject, and/or a zone with "ultimate" vision for which the difference defined before is smaller than half of the value of the global sensitivity parameter of the subject and/or a zone with acceptable vision for which the difference defined before is smaller than 1.5 times the value of the global sensitivity parameter of the subject.

It is also possible to use weighting: for instance, the angular zone in square degrees is calculated with a weighting coefficient that is determined from the ratio between the difference between the lens power and the subject's refraction and the value of the global sensitivity parameter of the subject.

For instance, the weight applied is 1 when said difference is 0; the weight is 0 when said difference is above the value of the global sensitivity parameter of the subject, and in between otherwise.

According to the invention, it is also possible to provide a performance map of the optical designs.

A performance score could be determined, for example by determining a global error W of the lens at each point of the surface of the lens. This performance score could be calculated with the following formula: $W = a \cdot (Sphlens - Sphsubject)^2 / Ssph^2 + b \cdot (Cyllens - Cylsubject)^2 / Scyl^2 + c \cdot (Axislens - Axisubject)^2 / Saxis^2$, with $a+b+c=1$ and a,b,c positive, where Sphlens-Sphsubject, Cyllens-Cylsubject and Axislens-Axisubject are the errors in sphere, cylinder and axis between the actual lens and the correction needed by the subject.

A global score may be obtained by integrating this score W on a region of the lens or the whole lens.

Such a performance map displays the tolerance of each optical design to a perturbation.

The probability of having a difference between the optical feature of the predetermined optical design and the adapted optical feature determined for the subject may be estimated as a function of the magnitude of the perturbation. The value of the global sensitivity parameter of the subject may be taken into account to adjust the determination of this probability: a probability of having a difference perceived by the subject between the optical feature of the optical design and the adapted optical feature determined for the subject is then determined and used.

The error tolerance values could then be adjusted as a function of the subject's sensitivity to errors.

Different global parameters may be taken into account for adjusting the error tolerance value of different optical feature: for example a sphere global sensitivity to sphere for the error tolerance to errors on the sphere or an overall global sensitivity to sphere and cylinder if these two optical features are taken into account.

For progressive lenses, a design for which variation of spherical power and astigmatism is faster, resulting in larger central clear zones of vision but with higher unwanted residual errors on the periphery, could be proposed for subjects with a value of global sensitivity parameter smaller than a threshold value (high sensitivity) and a design for which variation of spherical power and astigmatism is slower, resulting in reduced central clear zones of vision but with lower unwanted residual errors on the periphery, could be proposed for subjects with a value of global sensitivity parameter higher than a threshold value (low sensitivity).

Moreover, different other parameters of the subject could be taken into account for selecting the optical design of the lens, depending on the value of the global sensitivity parameter, such as a parameter relative to the visual behavior of the subject.

Such a parameter may be for example linked to the propensity of the subject to move his eyes or his head while performing a visual task.

This parameter relative to the visual behavior of the subject could be taken into account only for subjects having a global sensitivity parameter under a threshold value or could be taken into account with a weight determined as a function of the value of the global sensitivity parameter.

The invention also relates to a method for determining a customized optical design for the subject by taking into account the value of at least one global sensitivity parameter.

This customized optical design is obtained by modifying a predetermined optical design according to criteria based on the value of the global sensitivity parameter.

The optical design is for example optimized to reach target values for optical features of the corresponding lens, these target values being set taking into account the value of the global sensitivity parameter of the subject.

According to the invention, in the method for modifying a predetermined optical design for an ophthalmic lens in order to adapt it to the vision of a subject, said optical design comprises the current values of at least one optical feature of the corresponding lens associated with a plurality of gaze direction of the subject when the lens is worn by said subject. The method then comprises the following steps:
- determining a value of a global sensitivity parameter of a subject according to the method described above,
- determining an adapted value of said optical feature adapted to improve the vision of the subject,
- determining, for several gaze directions, the difference between the current value of the optical feature of the lens and the adapted value of said optical feature,
- comparing this difference with the value of the global sensitivity parameter of the subject,
- determining a modified optical design for a modified lens by modifying said predetermined optical design of the lens taking into account this comparison.

In practice, this is for example done by:
- determining a region of said predetermined optical design for which said difference is smaller than the value of the global sensitivity parameter of the subject,
- determining said modified optical design in order for a modified region of the modified optical design for which said difference is smaller than the value of the global sensitivity parameter of the subject to be larger than the corresponding region of the predetermined optical design and/or to have a shape closer to a predetermined shape. The modified optical design may for example be obtained by taking into account an additional treatment of the lens manufactured with the predetermined design: the modified optical design is then the optical design of the lens manufactured with the predetermined design to which the additional treatment is applied, for example an aspherization or atorization.

The application of the aspherization or atorization treatment may be adapted according to the value of at least one global sensitivity parameter, in order to obtain a zone of perfect vision with the largest size.

For example, the predetermined optical design may show a poor matching of one of the sphere of the lens with the adapted sphere determined for the subject. The zone of perfect vision of the lens manufactured with this optical design would then be small. Aspherization of the lens would enlarge the zone of perfect vision.

The choice to aspherize or not the lens may therefore depend on the value of at least one of the global sensitivity parameter of the subject. For example, if the value of the sphere or overall sensitivity parameter Sgsph or Soverall is below a predetermined threshold, the aspherization is recommended and/or performed.

The level of aspherization may also be adapted according to sensitivity: no aspherization for subjects with low sensitivity, aspherization with standard wearing parameters for subject with intermediate sensitivity and aspherization including fitting parameters such as tilt, wrap angle, eye-lens distance for subjects with high sensitivity.

The choice to atorize or not the lens may also depend on the value of at least one of the global sensitivity parameter of the subject. For example, if the value of the global cylinder or overall sensitivity parameter Sgcyl, SgJ0, SgJx0, Sgasr or Soverall is below a predetermined threshold, the atorization is recommended and/or performed.

Figure 9:
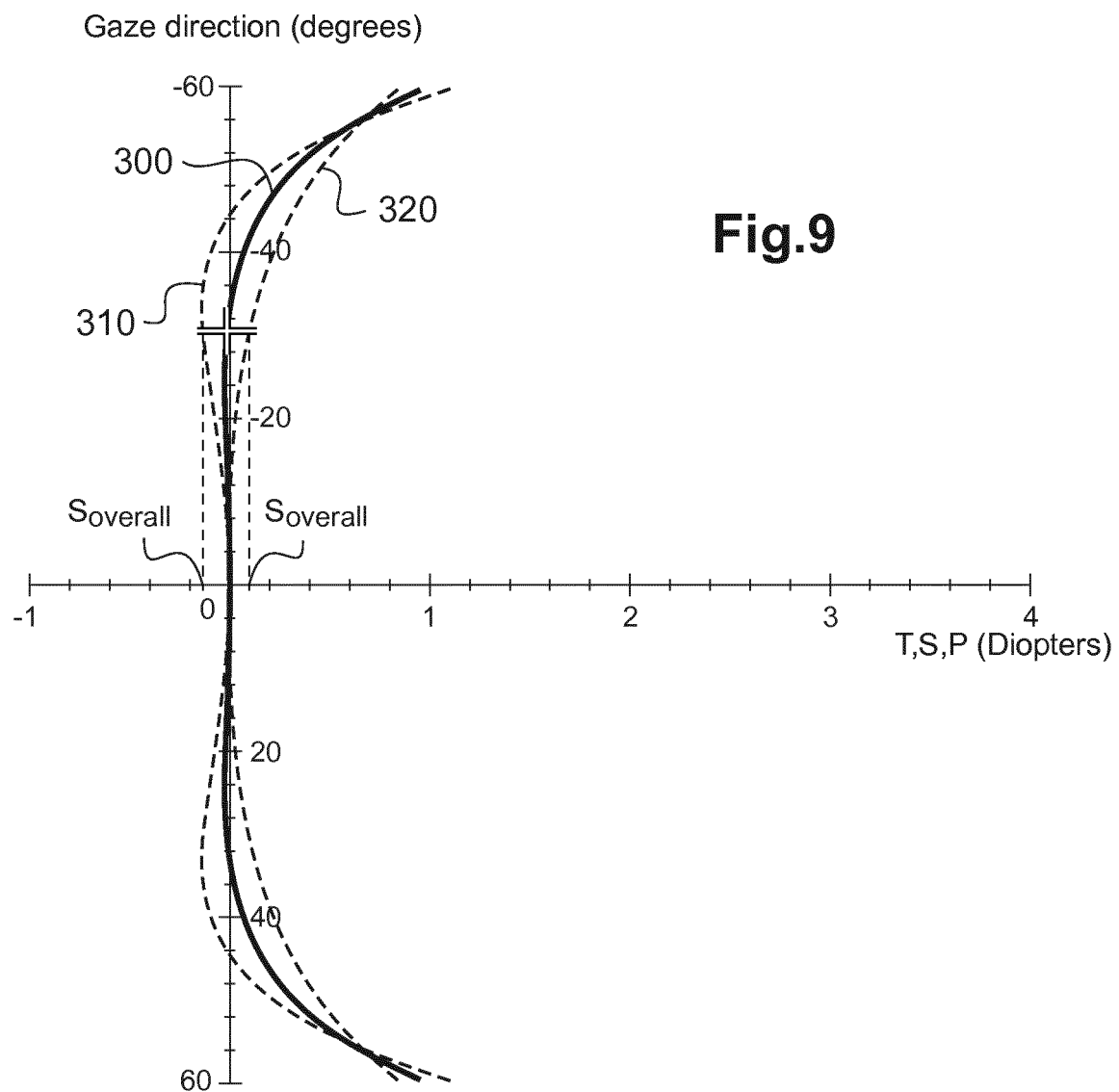
FIG. 9 is a graph showing the mean power, sagittal power and tangential power of a monofocal ophthalmic lens as a function of the angle of vision of the subject with a modified optical design for a subject having a high global sensitivity to sphere variation and low global sensitivity to cylinder variation.
Figure 10:
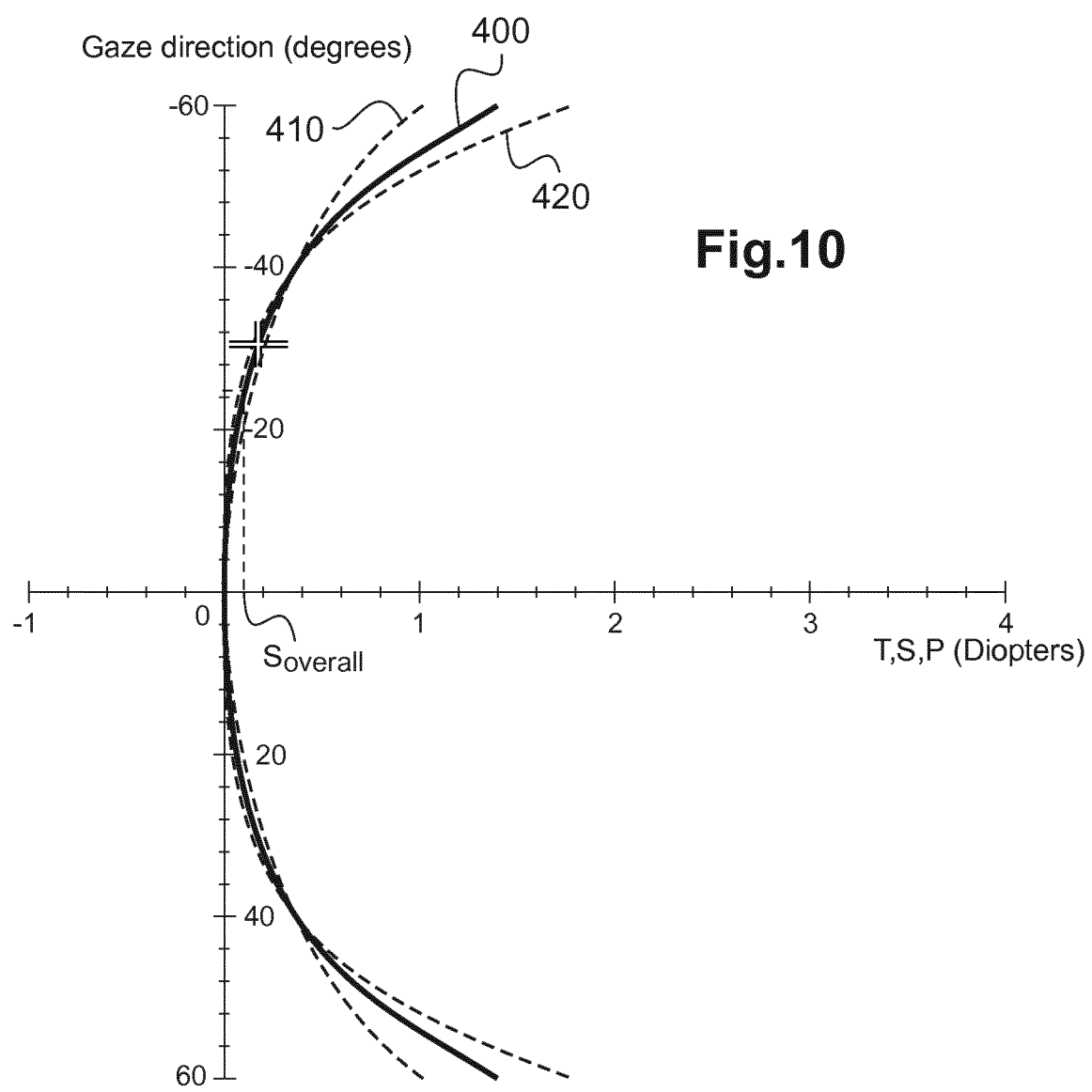
FIG. 10 is a graph showing the mean power, sagittal power and tangential power of a monofocal ophthalmic lens as a function of the angle of vision of the subject with a modified optical design for a subject having a high global sensitivity to cylinder variation and low global sensitivity to sphere variation.
Figure 11:
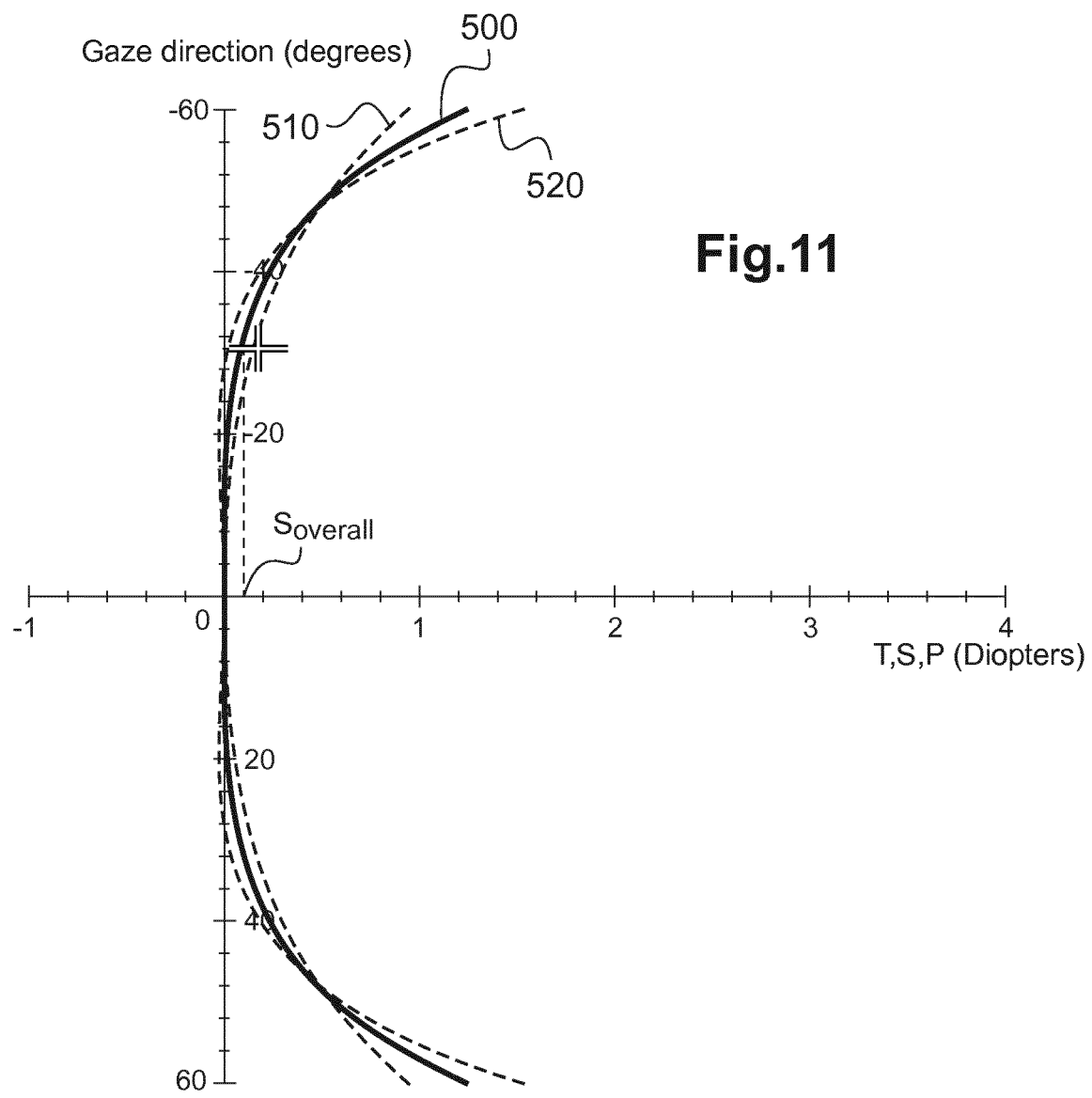
FIG. 11 is a graph showing the mean power, sagittal power and tangential power as a function of the angle of vision of the subject of a monofocal ophthalmic lens with a modified optical design for a subject having a high global sensitivity to cylinder variation and to sphere variation.

An example of possible modifications of a predetermined optical design according to the values of the sphere and cylinder global sensitivity parameter is shown on FIGS. 9 to 11.

Figure 8:
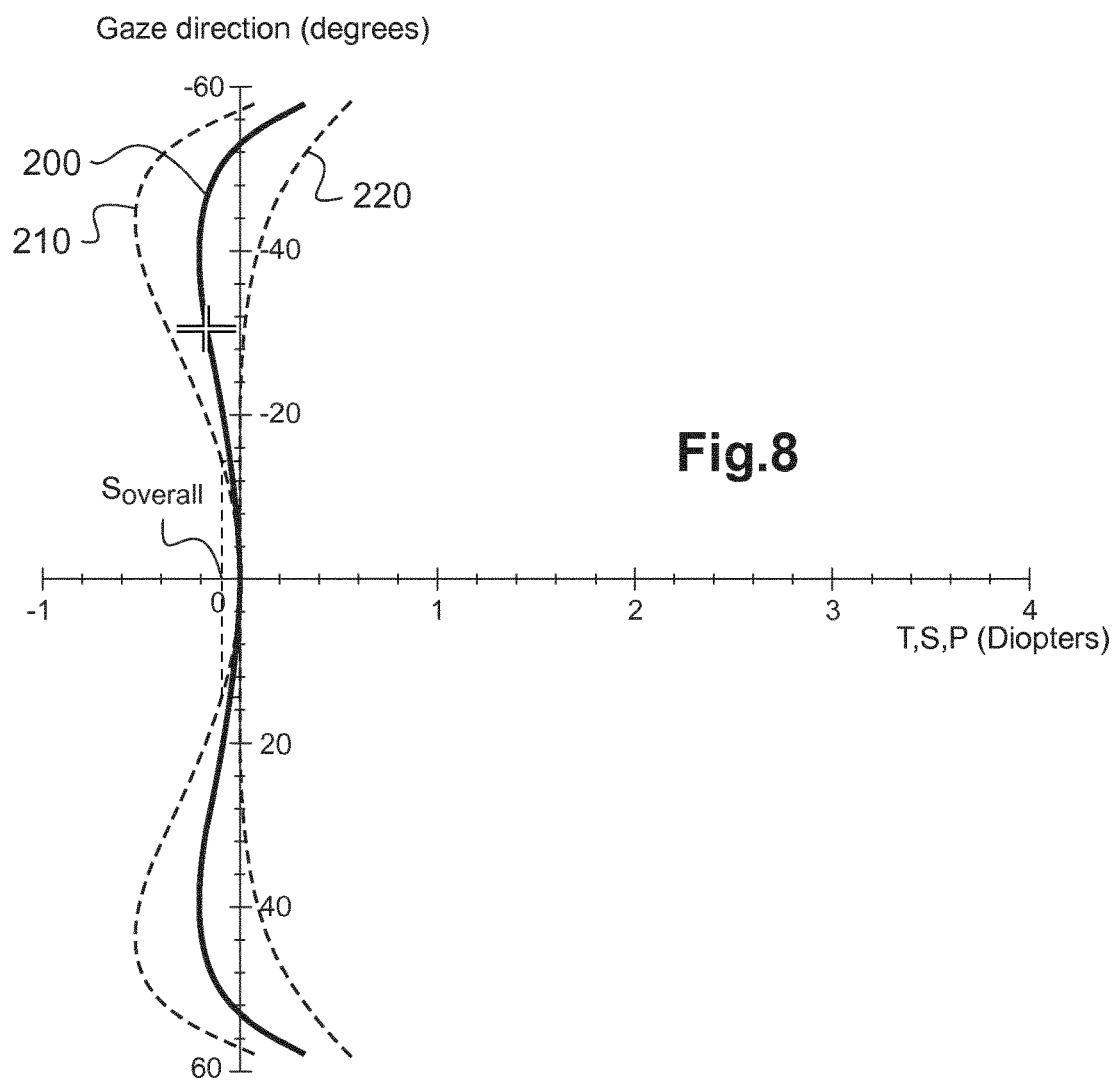
FIG. 8 is a graph showing the mean power, sagittal power and tangential power of a monofocal ophthalmic lens as a function of the angle of vision of the subject having a standard predetermined optical design.

FIG. 8 is a graph showing the mean power (full line curve 200), sagittal power and tangential power (dash lines curves 210, 220 on each side of the full line) of a monofocal ophthalmic lens having a predetermined optical design for different angle of vision of the subject (ordinate). This predetermined optical design is standard.

In the example of FIG. 8, the subject has a prescription for lenses having a sphere power of −4D. The lens is a standard single vision lens with refractive index 1.665 with a center thickness of 1.4 mm, with a spherical front surface in base curve (in 1.53) of 2.75D and a spherical back surface calculated in order to have −4D at the optical center. The wearing conditions of the lens are a cornea-lens distance of 12 mm, a pantoscopic tilt of 0° and a wrap angle of 0°. The prism between the two surfaces of the lens at the centre of the lens is 0. Here, the centre of the lens corresponds to gaze direction with angle 0° for the single vision lenses.

The optical center of the lens is placed at the angle of vision, or gaze direction angle equal to zero. The gaze directions are here measured along a vertical median plane of the lens. The angles of the gaze direction plotted in ordinate correspond to a vertical movement of the eye of the subject. The abscissa gives the error compared to the adapted optical feature, here the refraction power, for the subject. The abscissa zero therefore corresponds to an optical feature equal to the adapted optical feature of the subject.

The sagittal power and tangential power of the lens gives the maximal and minimal power of the lens for each gaze direction, taking into account the aberrations of the lens. The horizontal difference between this two curves gives the astigmatism of the lens at a given gaze direction.

It can be seen on the graph of FIG. 8 that with the predetermined optical design, the lens with the predetermined optical design will provide a perfect vision to the subject in a small area centered on the optical center. This area is in the angular range [−17, +17 degrees] if the global sensitivity Soverall of the subject is 0.1. Beyond this range, the curves parts from the axis of the ordinates, indicating that the powers of the lens differ from the adapted powers for the subject. At an eccentricity of 30° away from the optical center, the power error is −0.17 diopter (D) and the unwanted astigmatism is 0.39D.

According to the invention, the predetermined optical design of this lens may be modified, that is to say optimized, in order to have a larger zone around the optical center for which the subject will have a perfect vision with the lens.

If the subject has a high sensitivity to sphere and low sensitivity to cylinder, that is to say a value of the sphere global sensitivity Sgsph below a first sphere sensitivity threshold value and a value of the cylinder global sensitivity Sgcyl or SgJ0 or SJx0 above a first cylinder sensitivity threshold value, the modification of the predetermined optical design aims to reduce power error on a zone inside a circle of predetermined radius around the optical center, for example a 35° radius.

Threshold for high sensitivity is for example between 0.06D and 0.15D, preferentially 0.125D. Threshold for low sensitivity is for example between 0.125 and 0.375D, preferentially 0.15D A first modified design is obtained with these conditions for optimization.

The lens with the first modified optical design has the same refractive index, center thickness, front surface, wearing conditions and prism between its two surfaces as the standard lens, but the complex back surface is modified in order to reach the same optical characteristics (power and astigmatism errors in function of gaze directions) as a single vision lens with a front base curve of 4D instead of 2.75D. At an eccentricity of 30°, the power error of the lens with the first modified design is reduced to −0.02D and the unwanted astigmatism is reduced to 0.23D.

The graph of FIG. 9 shows the mean power 300, sagittal and tangential powers 310, 320 of this lens having the modified optical design with conventions similar to that of FIG. 8.

As can be seen on FIG. 9, the difference between the mean power curve 300, sagittal and tangential curves 310, 320 and the ordinate axis remains below the value of the global sensitivity parameter Soverall (0.1 D) in a range up to [−30, +30 degrees]. The zone with a perfect vision for the subject is indeed larger.

For a subject with a high sensitivity to cylinder and low sensitivity to sphere, that is to say with a value of the cylinder global sensitivity Sgcyl or SgJ0 or SgJx0 below a second cylinder sensitivity threshold value and a value of the sphere global sensitivity Sgsph above a second sphere sensitivity threshold value, the modification aims to reduce unwanted astigmatism at a minimum value on a zone inside a circle of predetermined radius around the optical centre, for example of 35° radius.

A second modified design is obtained with these conditions for optimization.

The lens with the second modified optical design has the same refractive index, center thickness, front surface, wearing conditions and prism between its two surfaces as the lens with the predetermined design, but the complex back surface is optimized in order to reach the same optical characteristics (power and astigmatism errors in function of gaze directions) as a single vision lens with a front base curve of 6D instead of 2.75D. At an eccentricity of 30°, the power error is now reduced to 0.17D and unwanted astigmatism is also reduced to 0.03D.

As can be seen on FIG. 10, the difference between the mean power curve 400, sagittal and tangential curves 410, 420 and the ordinate axis remains below the value of the global sensitivity parameter Soverall (0.1D) in a range up to [−22, +22 degrees]. The zone with a perfect vision for the subject is indeed larger than with the lens having the predetermined optical design.

For a subject with other sensitivities to cylinder and to sphere, the modification of the predetermined design aims to reduce a combination of both power error and unwanted astigmatism values on a zone inside a circle of predetermined radius around the optical centre, for example a 35° radius.

A third modified design is obtained with these conditions for optimization.

The lens with the third modified optical design has the same refractive index, center thickness, front surface wearing conditions and prism between its two surfaces as the standard lens, but the complex back surface is optimized in order to reach the same optical characteristics (power and astigmatism errors in function of gaze directions) as a single vision lens with a front base curve of 5D instead of 2.75D. At an eccentricity of 30° the power error is now reduced to 0.09D and unwanted astigmatism is also reduced to 0.12D.

As can be seen on FIG. 11, the difference between the mean power curve 500, sagittal and tangential curves 510, 520 and the ordinate axis remains below the value of the global sensitivity parameter Soverall (0.1D) in a range up to [−30, +30 degrees]. The zone with a perfect vision for the subject is indeed larger than with the lens having the predetermined optical design.

As shown in the examples above, several values of different global sensitivity parameters may be taken into account for optimizing the optical design of the lens.

Usually single vision lenses are calculated according to the subject's prescription and can be optimized taking into account the prescription. This optimization represents a compromise between reducing power error and reducing unwanted astigmatism on the entire lens. With the measure of the subject sensitivity to sphere (Sgsph) and to cylinder (Sgcyl) it is possible to adjust the optimization according to the subject sensitivities.

Optical designs of progressive lenses may also be modified for optimization according to the value of at least one global sensitivity parameter.

In a progressive lens, the modification of the design will aim to enlarge the zones of perfect vision centered on the far vision point and near vision point of the lens.

The higher is the subject's sensitivity, that is the lower is the value of the global sensitivity parameter, the larger will be the zones of vision through the lens with low aberrations levels.

Figure 12:
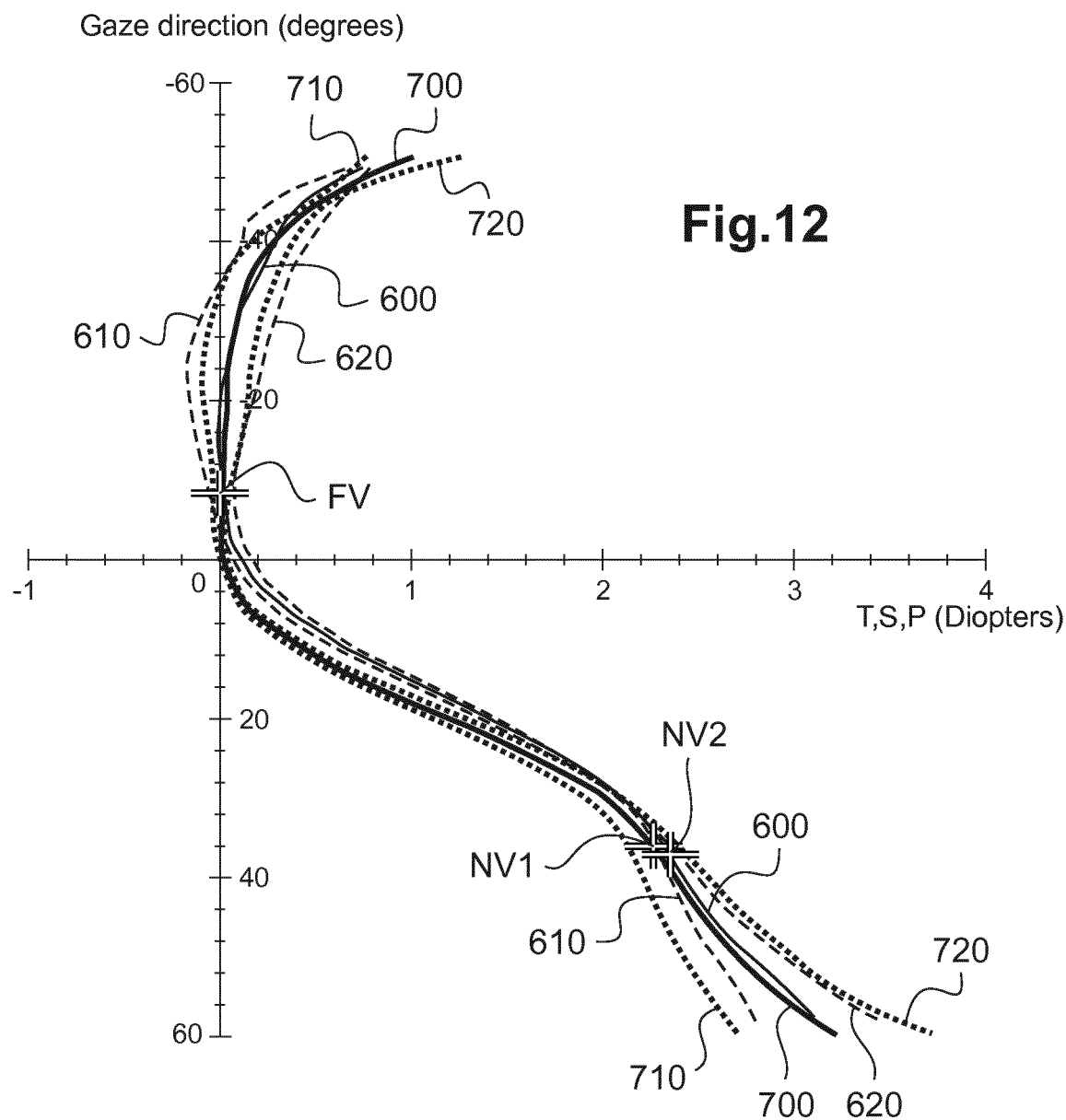
FIG. 12 is a graph showing the mean power, sagittal power and tangential power as a function of the vertical angle of vision ALPHA, also called vertical declination gaze angle, of the subject of a multifocal ophthalmic lens with a modified optical designs for a subject having a low (dashed and thin full lines) or a high (dotted and thick full lines) global sensitivity.
Figure 13:
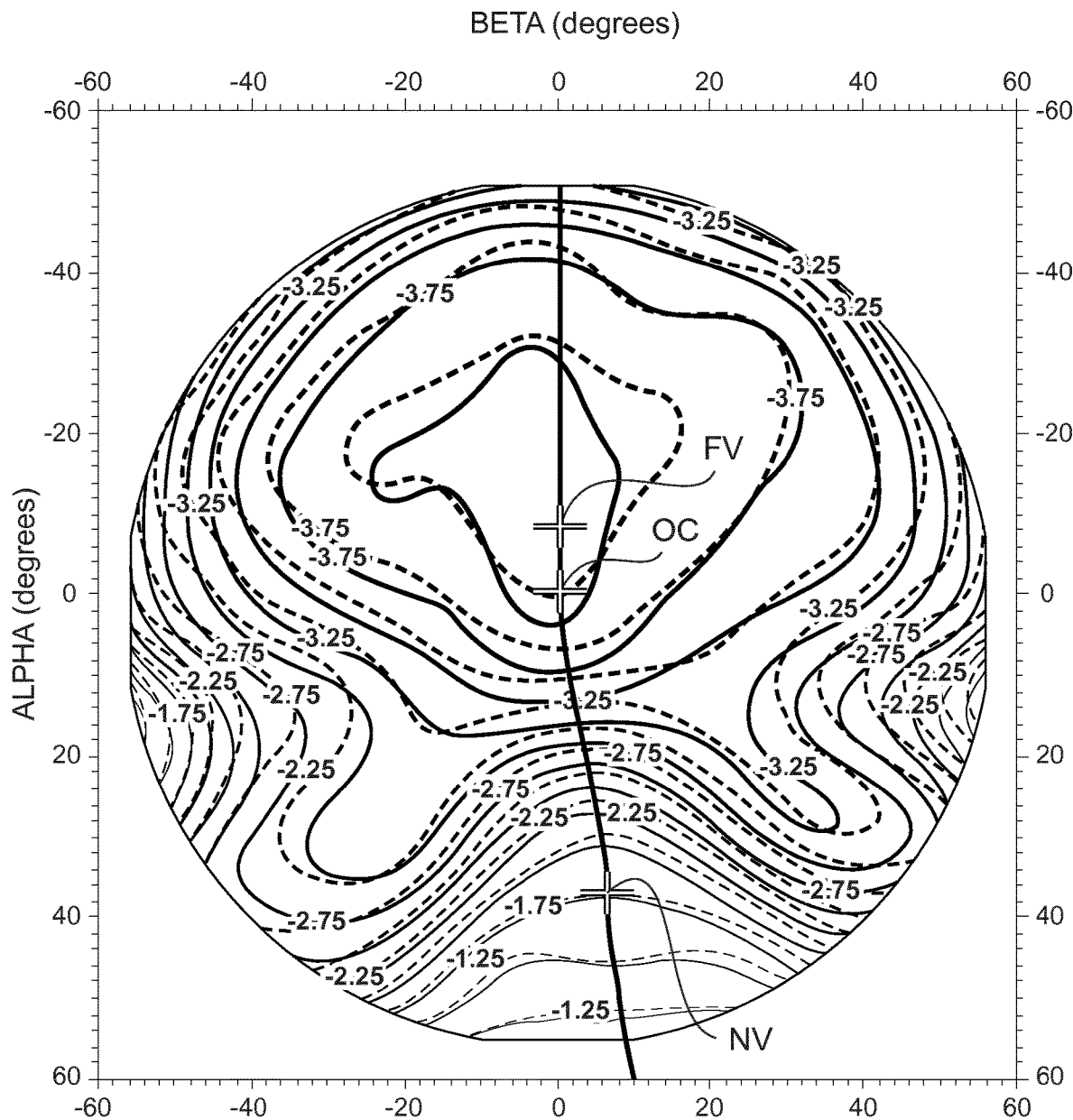
FIGS. 13 and 14 are graphs showing the lines with same mean power (FIG. 13) or same unwanted astigmatism (FIG. 14) of the lenses having the optical designs of FIG. 12: modified optical designs for a subject having a low (dashed lines) or a high (full lines) global sensitivity.
Figure 14:
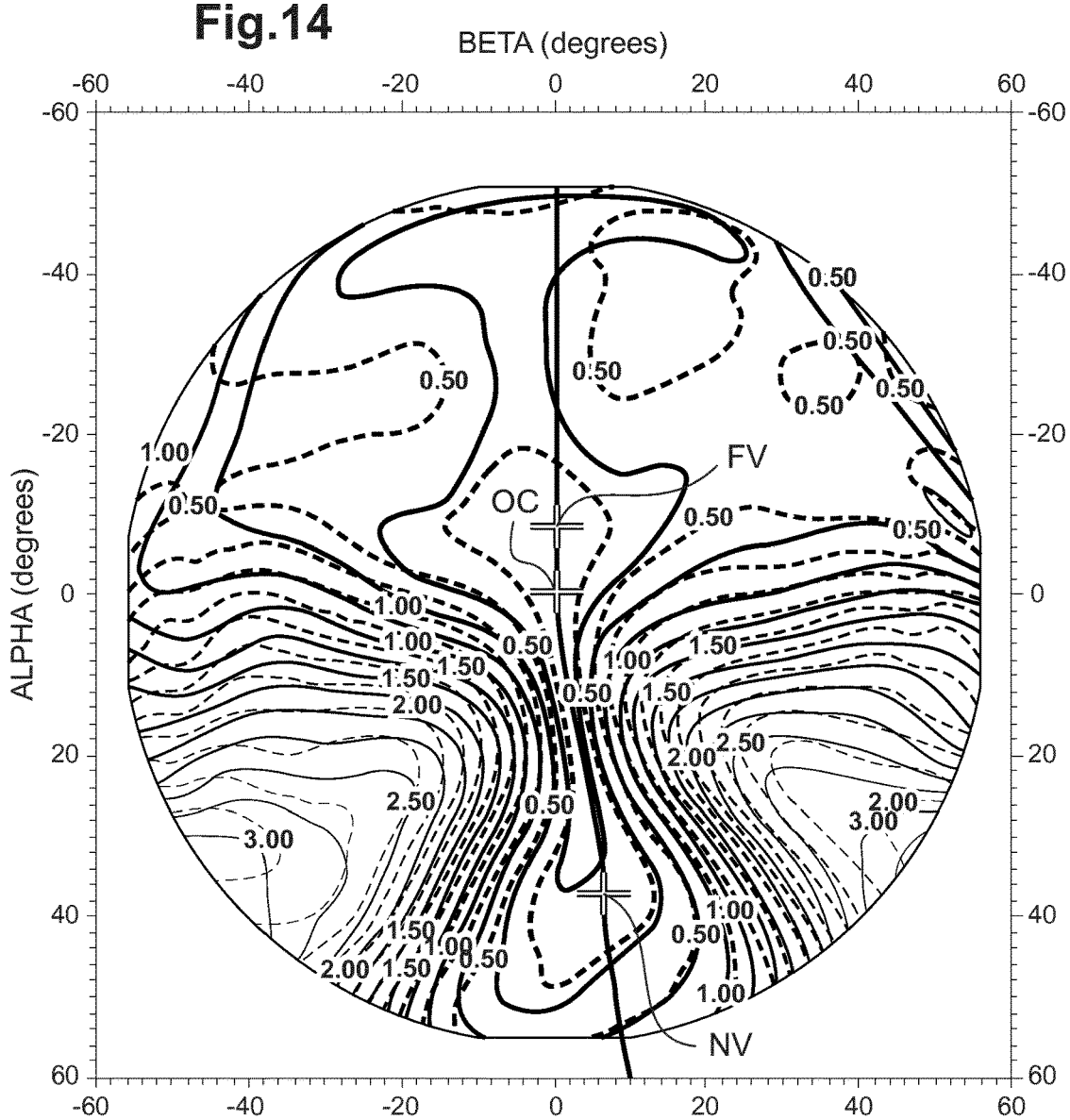

The size of vision zones with low levels of power error and unwanted astigmatism can be modified according to the score of global sensitivity. In the example of FIGS. 12 to 14, the subject has a far vision prescription of −4D and an addition prescribed of +2D. The progressive lens has a refractive index of 1.665 with a center thickness of 1.4 mm, and a spherical front surface in base curve (in 1.53) of 2.75D.

The wearing conditions of the lens are a cornea-lens distance of 12 mm, a pantoscopic tilt of −8° and a wrap angle of 0°. The prism between the two surfaces of the lens at the Prism Reference Point corresponding to ⅔ of the addition. The Prism Reference Point is located between the two micro-circles marked on a progressive lens. It corresponds to a point located 4 mm below the fitting cross which is placed in front of the pupil of the subject eye and is at gaze angle 0°.

It is for example possible to modify a predetermined optical design of this lens to optimize the far vision zone of the lens, that is increase the size of the perfect vision zone centered on the far vision point, taking into account the value of the global sensitivity parameter of the subject. Here, the global sensitivity parameter Soverall is taken into account.

On FIG. 12, the dashed and thin full lines 600, 610, 620 represent the optical features (sagittal and tangential powers, mean power) of the lens optimized for a subject with a low sensitivity, that is to say a value of the global sensitivity parameter above a fourth threshold, and dotted and thick full lines in 700, 710, 720 is represented the optical features (sagittal and tangential powers, mean power) of the lens optimized for a subject with the same prescription but with very high sensitivity, that is to say a value of the global sensitivity parameter below a fifth threshold. The high value of the global sensitivity parameter denotes a low sensitivity and a low value of the global sensitivity parameter denotes a high sensitivity.

In the far vision zone, located at cross FV on FIGS. 12 to 14, the mean power has been stabilized in a slightly wider zone and the low unwanted astigmatism zone has been enlarged for the optical design optimized for the subject with high sensitivity.

The optical centre is referenced OC on FIGS. 13 and 14. On these FIGS. 13 and 14, ALPHA and BETA are the vertical and horizontal gaze direction angle.

Sensitivity may also be taken into account as a tolerance during manufacturing and/or edging/mounting process.

In particular, as described above, the value of the global parameter determined according to the method of the invention may be used to adapt the test protocol implemented to determine the refraction features of the subject's eye and the refraction features of the corrective lenses needed by this subject.

The eye care professional is informed of this value by a message displayed on a screen of the device used for determining the refraction. A visual or sound warning signal may be emitted to attract the attention of the eye care professional on this information. An alert signal may also be emitted depending on the value determined. For example, an alert signal is emitted for subject whose sensitivity is over a predetermined threshold, for example for values of global sensitivity parameter under 0.05 D.

Based on this value of the global sensitivity parameter, recommendations may be made to the eye care professional regarding the test protocol for determining the refraction features of the subject. For example, the use of a specific instrument may be recommended, for example an instrument providing precise measurement such as a refractor placed on a column, for a subject with high sensitivity.

The value of the global sensitivity determined for the subject may also be used by the eye care practitioner to make recommendation to the subject. Theses recommendations are made for example while handing the prescription to the subject. They may be adapted in view of the comparison of the value of the global sensitivity parameters with thresholds values.

The value of the global sensitivity parameter may also be indicated of the prescription and may be underlined if it is in a predetermined range of values.

Among the possible recommendations linked to the value of the global sensitivity parameter, it is possible to consider recommending a type of lens: for example, accurate lenses should be recommended to subjects with a high global sensitivity in order to provide accurate dioptric features to the subject.

It is moreover possible to estimate the visual performance of the subject with a given type of lens as a function of the refraction features adapted to the wearer and his global sensitivity. Such estimated visual performance would take into account the predicted power error and resulting astigmatism linked to the optical aberrations of the lens. The visual performances could be simulated and shown to the subject.

A type of frame could also be recommended based on the value of the global sensitivity parameter: a subject with a high global sensitivity would benefit from a frame that can be precisely fitted on his face, and that stays in place once fitted. It is for example the case of frames with nose pads.

As already mentioned above, the optical design of the lens may also be modified based on the value of the global sensitivity parameter, as well as the manufacturing, cutting, mounting and checking steps of the process of providing a visual correction equipment. When the lab in charge for manufacturing the lens receives the order, which comprises the value of the global sensitivity parameter of the subject, the lab may check the feasibility of the lens ordered and confirm the order, or send instead a request for additional parameter measurement on the subject, or the indication of an additional delay needed to achieve the order, based on the value of the global sensitivity parameter and the level of precision needed in manufacturing the lens.

Final adjustment of the equipment at delivery in optician stores may also be adapted: special care may be taken for fitting the eyeglasses on the face of the subject depending on the value of the global sensitivity parameter: a highly sensitive subject will require an accurate fitting.

Final recommendations may include recommending to subjects having a high sensitivity to come in regularly to check and adjust the fitting of the eyeglasses and also to check the current refraction of the eyes of the subject, with a test protocol adapted to the value of the sensitivity parameter.

Highly sensitive subject would need an accurate control of frame adjustment or re-measurement of fitting parameters whereas subjects with low sensitivity will not benefit from it.

The commercial offers made to the subject may also be adapted as a function of the value of the global sensitivity parameter. For example, a subject with a high sensitivity who needs to get new equipment more often than a subject with a low sensitivity could get specific commercial offers.

In order for the value of the global sensitivity parameter to be taken into account all along the process for providing accurate visual correction equipment, this value has to be transmitted to all the actors involved in this process.

To this end, the value of the global sensitivity parameter is associated with an identification tag of the subject. The association of the two data is for example stored on a server accessible online in a secure manner. It may be stored on Eyecloud™, a service provided by the Applicant.

Known method of encryption may be used in order to provide security of the data.

The methods taking into account the value of a global sensitivity parameter described here may improve image quality, comfort and/or adaptation of the subject to the lens.

Alternatively, any method described here using the global sensitivity parameter may be implemented, in a simplified mode, with single values of specific sensitivity parameters. However, the single values of the specific sensitivity parameters being less accurate and reliable, the improvements will be inferior compared to the improvements made using the global sensitivity parameter values.

The invention claimed is:

1. A method for determining a value of a global sensitivity parameter of a subject, said global sensitivity parameter being relative to the sensitivity of said subject to a variation of at least a dioptric optical feature of at least an ophthalmic lens placed in front of at least one eye of said subject, comprising the following steps:
   a) determining (100) a single value of at least a first sensitivity parameter of said subject, relative to the sensitivity of the subject to a variation of a first dioptric optical feature of at least a first ophthalmic lens,
   b) determining (110) a single value of at least a second sensitivity parameter of said subject, relative to the sensitivity of the subject to a variation of a second dioptric optical feature of at least a second ophthalmic lens,
   each of the first and second sensitivity parameters being respectively related to the smallest variation of said first and second dioptric optical features that may be perceived by the subject,
   c) using computing means to determine (120) said value of the global sensitivity parameter taking into account a combination of said single values of the first and second sensitivity parameters.

2. The method according to claim 1, wherein said at least a first and second sensitivity parameter determined in steps a) and b) each comprises at least one of the following:
sphere sensitivity to the variation of sphere of said at least a first or second ophthalmic lens for at least one of the eyes of said subject,
cylinder and/or axis sensitivity to the variation of cylinder power and/or axis of said at least a first or second ophthalmic lens for at least one of the eyes of the subject,
sphere binocular sensitivity of said subject to the binocular variation of the sphere of the first and second ophthalmic lenses,
binocular balance sensitivity of the subject to a variation in binocular balance of the first and second ophthalmic lenses,
addition sensitivity to the variation in the addition of said at least a first or second ophthalmic lens for at least one of the eyes of the subject.

3. The method according to claim 2, wherein said single values of at least a first and second sensitivity parameter determined in steps a) and b) are each determined with different measuring methods or each determined in similar or different measurement conditions.

4. The method according to claim 3, wherein, in step c), said combination comprises a mean of the single values of the first and second sensitivity parameters determined during steps a) and b).

5. The method according to claim 3, wherein the single values of the first and second sensitivity parameters determined during steps a) and b) are either:
single values of the cylinder sensitivities of each of the left and right eyes
or
single values of the axis sensitivities of each of the left and right eyes,
or
single values of astigmatism sensitivities of each of the left and right eyes,
single values of the sphere, cylinder, axis and binocular balance sensitivities of one of the left and right eyes,
and, in step c), the value of the global sensitivity parameter determined is respectively
the value of a global cylinder sensitivity parameter equal to the mean value of the single values of the cylinder sensitivities of the left and right eyes
or
the value of a global axis sensitivity parameter equal to a mean value of the single values of the axis sensitivities of the left and right eyes
or
the value of a global left or right eye sensitivity parameter equal to the mean value of the single values of the sphere, cylinder, axis and binocular balance sensitivities of the left or right eye.

6. The method according to claim 2, wherein, in step c), said combination comprises a mean of the single values of the first and second sensitivity parameters determined during steps a) and b).

7. The method according to claim 2,
wherein the single values of the first and second sensitivity parameters determined during steps a) and b) are either:
single values of the cylinder sensitivities of each of the left and right eyes
or
single values of the axis sensitivities of each of the left and right eyes,
or
single values of astigmatism sensitivities of each of the left and right eyes,
single values of the sphere, cylinder, axis and binocular balance sensitivities of one of the left and right eyes,
and, in step c), the value of the global sensitivity parameter determined is respectively
the value of a global cylinder sensitivity parameter equal to the mean value of the single values of the cylinder sensitivities of the left and right eyes
or
the value of a global axis sensitivity parameter equal to a mean value of the single values of the axis sensitivities of the left and right eyes or
the value of a global left or right eye sensitivity parameter equal to the mean value of the single values of the sphere, cylinder, axis and binocular balance sensitivities of the left or right eye.

8. The method according to claim 1, wherein, in step c), said combination comprises a mean of the single values of the first and second sensitivity parameters determined during steps a) and b).

9. The method according to claim 8,
wherein the single values of the first and second sensitivity parameters determined during steps a) and b) are either:
single values of the cylinder sensitivities of each of the left and right eyes
or
single values of the axis sensitivities of each of the left and right eyes,
or
single values of astigmatism sensitivities of each of the left and right eyes,
single values of the sphere, cylinder, axis and binocular balance sensitivities of one of the left and right eyes,
and, in step c), the value of the global sensitivity parameter determined is respectively
the value of a global cylinder sensitivity parameter equal to the mean value of the single values of the cylinder sensitivities of the left and right eyes
or
the value of a global axis sensitivity parameter equal to a mean value of the single values of the axis sensitivities of the left and right eyes
or
the value of a global left or right eye sensitivity parameter equal to the mean value of the single values of the sphere, cylinder, axis and binocular balance sensitivities of the left or right eye.

10. The method according to claim 1, wherein the single values of the first and second sensitivity parameters determined during steps a) and b) are either:
single values of the cylinder sensitivities of each of the left and right eyes
or
single values of the axis sensitivities of each of the left and right eyes,
or
single values of astigmatism sensitivities of each of the left and right eyes,
single values of the sphere, cylinder, axis and binocular balance sensitivities of one of the left and right eyes,
and, in step c), the value of the global sensitivity parameter determined is respectively the value of a global cylinder sensitivity parameter equal to the mean value of the single values of the cylinder sensitivities of the left and right eyes or the value of a global axis sensitivity parameter equal to a mean value of the single values of the axis sensitivities of the left and right eyes or the value of a global left or right eye sensitivity parameter equal to the mean value of the single values of the sphere, cylinder, axis and binocular balance sensitivities of the left or right eye.

11. The method according to claim 1, wherein, during steps a) and b), single values of the sphere sensitivity of each of the left and right eyes of the subject and a single value of the sphere binocular sensitivity of said subject are determined, and, in step c), the value of the global sensitivity parameter determined is the value of a global sphere sensitivity parameter equal to a mean value of the single values of the sphere sensitivities of the left and right eyes and of the sphere binocular sensitivity.

12. The method according to claim 1, wherein, during steps a) and b), the following are determined:

single values of the sphere sensitivities of each of the left and right eyes, and single values of the cylinder sensitivities of each of the left and right eyes, and single values of the axis sensitivities of each of the left and right eyes, and a value of the sphere binocular sensitivity of said subject, and a value of the binocular balance sensitivity of said subject, and in step c), a value of a final global sensitivity parameter is determined with the following equation:

$$\text{Soverall} = [(\text{SsphOD} + \text{SsphOG} + \text{Ssphbino})/3 + (\text{ScylOD} + \text{ScylOG})/2 + (\text{SaxOD} + \text{SaxOG})/2 + \text{Seqbino}]/4,$$ where, Soverall is the global sensitivity parameter of the subject, SsphOD is the single value of the sphere sensitivity of the right eye of the subject, SsphOG is the single value of the sphere sensitivity of the left eye of the subject, Ssphbino is the value of the sphere binocular sensitivity of said subject, ScylOD is the single value of the cylinder sensitivity of the right eye of the subject, ScylOG is the single value of the cylinder sensitivity of the left eye of the subject, SaxOD is the single value of the axis sensitivity of the right eye of the subject, SaxOG is the single value of the axis sensitivity of the left eye of the subject, and Seqbino is the value of the binocular balance sensitivity of the subject.

13. The method according to claim 1, wherein, in step c), said combination comprises a weighted mean value of the single values of the first and second sensitivity parameters determined during steps a) and b), the weights associated to the values of the first and second sensitivity parameters depending on:

a usual visual behavior of the subject, and/or a type of lens to be worn by the subject, and/or activities that the subject wishes to have with the lens, and/or an eye dominance data, and/or an assessment of the comfort of a current/previous lens worn by the subject, and/or data indicated on the previous prescription for an optical correction equipment.

14. The method according to claim 1, further comprising a step of:

displaying this value of the global sensitivity parameter for informing an eye care practitioner.

15. The method for determining an adapted dioptric optical feature of an ophthalmic lens according to claim 14, wherein said incremental value is determined to minimize the difference between this incremental value and the value of the global sensitivity parameter.

16. A method for determining an adapted dioptric optical feature of an ophthalmic lens adapted to improve the vision of a subject, comprising the following steps:

performing a test protocol comprising repeated steps of:
placing a test lens in front of an eye of the subject,
assessing the quality of vision of the subject looking through said test lens, the value of the dioptric optical feature of the test lens being incremented by an incremental value between each repetition of said steps, comparing the quality of vision of the subject looking through at least two successive test lenses placed in front of the eye of the subject during two successive repetitions of said steps of the test protocol, and determining said adapted dioptric optical feature based on this comparison, determining a value of a global sensitivity parameter of a subject according to the method of claim 1, determining said incremental value taking into account this value of the global sensitivity parameter.

17. A method for selecting an appropriate optical design for an ophthalmic lens adapted to improve the vision of a subject, among a list of predetermined optical designs, said optical design comprising current values of at least one dioptric optical feature of the corresponding lens having said predetermined optical design, associated with a plurality of gaze directions of the subject when the lens is worn by said subject, comprising the following steps:

determining a value of a global sensitivity parameter of a subject according to the method of claim 1, determining an adapted value of said dioptric optical feature adapted to improve the vision of the subject, determining, for different gaze directions, the difference between the current value of the dioptric optical feature of the corresponding lens and the adapted value of said dioptric optical feature, comparing this difference with the value of the global sensitivity parameter of the subject, selecting, among said list of predetermined optical designs, the appropriate optical design taking into account this comparison.

18. A method for modifying a predetermined optical design for an ophthalmic lens in order to adapt the ophthalmic lens to the vision of a subject, said optical design comprising the current values of at least one dioptric optical feature of a corresponding lens having said predetermined optical design, associated with a plurality of gaze directions of the subject when the lens is worn by said subject, comprising the following steps:

determining a value of a global sensitivity parameter of a subject according to the method of claim 1, determining an adapted value of said dioptric optical feature adapted to improve the vision of the subject, determining, for several gaze directions, the difference between the current value of the dioptric optical feature of the corresponding lens and the adapted value of said dioptric optical feature, comparing this difference with the value of the global sensitivity parameter of the subject, determining a modified optical design for a modified corresponding lens by modifying said predetermined optical design of the lens taking into account this comparison.

19. A system for determining a value of a global sensitivity parameter of a subject, said global sensitivity parameter being relative to the sensitivity of said subject to a variation of at least a dioptric optical feature of at least an ophthalmic lens placed in front of at least one eye of said subject, comprising:

means for determining a single value of at least a first sensitivity parameter of said subject, relative to the sensitivity of the subject to a variation of a first dioptric optical feature of at least a first ophthalmic lens, means for determining a single value of at least a second sensitivity parameter of said subject, relative to the sensitivity of the subject to a variation of a second dioptric optical feature of at least a second ophthalmic lens, computing means programmed for determining said value of the global sensitivity parameter taking into account a combination of said single values of the first and second sensitivity parameters.

20. The system according to claim 19, further comprising means for storing said value of the global sensitivity parameter determined by the computing means, and/or means for displaying said value of the global sensitivity parameter determined by the computing means.

* * * * *